(12) United States Patent
Foricher et al.

(10) Patent No.: US 9,102,628 B2
(45) Date of Patent: Aug. 11, 2015

(54) DERIVATIVES OF PYRAZOLE 3,5-CARBOXYLATES, THEIR PREPARATION AND THEIR APPLICATION IN THERAPEUTICS

(75) Inventors: Yann Foricher, Paris (FR); Martin Smrcina, Tucson, AZ (US); Viviane Van Dorsselaer, Paris (FR); Fabienne Weber, Paris (FR)

(73) Assignee: SANOFI, Paris (FR)

( * ) Notice: Subject to any disclaimer, the term of this patent is extended or adjusted under 35 U.S.C. 154(b) by 937 days.

(21) Appl. No.: 12/647,056

(22) Filed: Dec. 24, 2009

(65) Prior Publication Data

US 2010/0160377 A1 Jun. 24, 2010

Related U.S. Application Data

(63) Continuation of application No. PCT/FR2008/001028, filed on Jul. 15, 2008.

(60) Provisional application No. 60/949,950, filed on Jul. 16, 2007.

(30) Foreign Application Priority Data

Jul. 16, 2007 (FR) ...................... 07 05123

(51) Int. Cl.
| | |
|---|---|
| *C07D 403/02* | (2006.01) |
| *C07D 233/22* | (2006.01) |
| *C07D 401/00* | (2006.01) |
| *C07D 413/00* | (2006.01) |
| *A61K 31/535* | (2006.01) |
| *A61K 31/445* | (2006.01) |
| *A61K 31/415* | (2006.01) |
| *C07D 231/14* | (2006.01) |
| *C07D 401/06* | (2006.01) |
| *C07D 401/14* | (2006.01) |
| *C07D 403/06* | (2006.01) |

(52) U.S. Cl.
CPC ............ *C07D 231/14* (2013.01); *C07D 401/06* (2013.01); *C07D 401/14* (2013.01); *C07D 403/06* (2013.01)

(58) Field of Classification Search
None
See application file for complete search history.

(56) References Cited

FOREIGN PATENT DOCUMENTS

WO 03/040096 5/2003

OTHER PUBLICATIONS

Bambal., R., et. al., Synthesis of Nε-(p-Bromophenyl)-L-Lysine and Nr(p-Bromophenyl)-L-Histidine as Models for Adducts of Bromobenzene 3,4-Oxide to Protein. Observation of an Unusual Pd-Catalyzed Nr- to Nr-Aryl Substituent Migration, J. Org. Chem., (1994), vol. 59, pp. 729-732.

Bertus, P., et. al., A Direct Synthesis of 1-Aryl- and 1-Alkenylcyclopropylamines from Aryl and Alkenyl Nitriles, J. Org. Chem., (2003), vol. 68, pp. 7133-7136.

Ciganek, E., et. al., Tertiary Carbinamines by Addition of Organocerium Reagents to Nitriles, J. Org. Chem., vol. 57, pp. 4521-4527, (1992).

Colyer, J. T., et. al., Reversal of Diastereofacial Selectivity in Hydride Reductions of N-Tert-Butanesulfinyl Imines, J. Org. Chem., (2006), vol. 71, pp. 6859-6862.

Cossy, J., et. al., Regioselective Ring Opening of Epoxides by Nucleophiles Mediated by Lithium Bistrifluoromethanesulfonimide, Tetrahedron Letters, vol. 43, pp. 7083-7086, (2002).

Ghosh, A. K., et. al., Stereoselective Photochemical 1,3-Dioxolane Addition to 5-Alkoxymethyl-2(5H)-Furanone: Synthesis of Bis-Tetrahydrofuranyl Ligand for HIV Protease Inhibitor UIC-94017 (TMC-114), J. Org. Chem., (2004). vol. 69, pp. 7822-7829.

Haque, T. S., et. al., Parallel Synthesis of Potent, Pyrazole-Based Inhibitors of *Helicobacter pylori* Dihydroorotate Dehydrogenase, J. Med. Chem., (2002), vol. 45, pp. 4669-4678.

Hassan, J. , Aryl-Aryl Bond Formation One Century after the Discovery of the Ullmann Reaction, Chem. Rev. 2002, 102, pp. 1359-1469.

Klapars, A., et. al., A General and Efficient Copper Catalyst for the Amidation of Aryl Halides and the N-Arylation of Nitrogen Heterocycles, J. Am. Chem. Soc. (2001), vol. 123, pp. 7727-7729.

Luly, J. R., et. al., A Synthesis of Protected Aminoalkyl Epoxides from a-Amino Acids, J. Org. Chem., (1987), vol. 52, pp. 1487-1492.

(Continued)

*Primary Examiner* — Nyeemah A Grazier
(74) *Attorney, Agent, or Firm* — Morrison & Foerster LLP

(57) ABSTRACT

The invention relates to derivatives of pyrazole 3,5-carboxylates, of general formula (I):

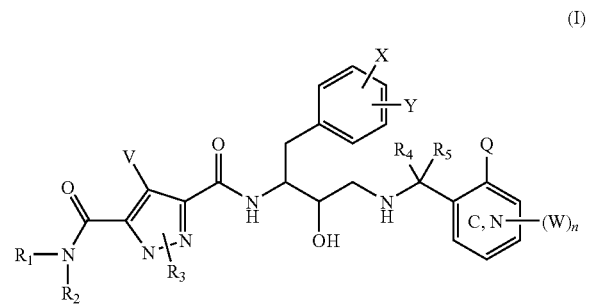

in which $R_1$, $R_2$, $R_3$, $R_4$, $R_5$, X, Y, V, W and n are as defined herein. The invention also relates to salts of these compounds as well as hydrates or of solvates, enantiomers, diastereoisomers and mixtures thereof. Also disclosed are the methods of preparation and application in therapeutics of compounds of formula (I).

21 Claims, No Drawings

(56) References Cited

OTHER PUBLICATIONS

Wolfe, M. S., et. al., Secretase Targets for Alzheimer's Disease: Identification and Therapeutic Potential, Journal of Medicinal Chemistry, vol. 44, No. 13, (2001), pp. 2039-2060.

Kuo, S-C., et. al., Studies of Heterocyclic Compounds. 6.1 Synthesisi and Analgesic and Antiinflammatory Activities of 3,4-Dimethylpyrano[2,3-c]Pyrazol-6-One Derivatives, J. Med. Chem., (1984), vol. 27, pp. 539-544.

Holscher, C., et. al., Development of Beta-Amyloid-Induced Neurodegeneration in Alzherimer's Disease and Novel Neuroprotective Strategies, Reviews in the Neurosciences, vol. 16, pp. 181-212, (2005).

Hussain, I., et. al., Oral Administration of a Potent and Selective Non-Peptidic BACE-1 Inhibitor Decreases B-Cleavage of Amyloid Precursor Protein and Amyloid-B Production In Vivo, Journal of Neurochemistry, vol. 100, pp. 802-809, (2007).

Coria, F., et. al., Cerebral Amyloid Angiopathiss, Neuropathology and Applied Neurobiology, (1996), vol. 22, pp. 216-227.

DERIVATIVES OF PYRAZOLE 3,5-CARBOXYLATES, THEIR PREPARATION AND THEIR APPLICATION IN THERAPEUTICS

This application is a continuation of International application No. PCT/FR2008/001,028, filed Jul. 15, 2008, which is incorporated herein by reference in its entirety; which claims the benefit of U.S. Provisional Application No. 60/949,950, filed Jul. 16, 2007, and the benefit of priority of French patent application Ser. No. 07/05,123, filed Jul. 16, 2007.

The present invention relates to derivatives of pyrazole 3,5-carboxylates, their preparation and their applications in therapeutics.

It has been found that these compounds, derived from pyrazole 3,5-carboxylates, are inhibitors of β-secretase BACE1 (β-site amyloid precursor protein cleavage enzyme subtype 1).

The present invention relates to compounds corresponding to formula (I):

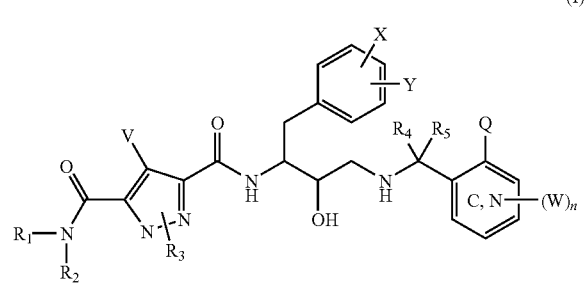

in which
- $R_1$ represents a hydrogen atom, a $C_{3-6}$-cycloalkyl group, $C_{1-6}$-alkyl group, said $C_{1-6}$-alkyl optionally being substituted with one or more groups selected from hydroxy, $C_{1-6}$-alkoxy, halogen, $CF_3$, or $OCF_3$;
- $R_2$ represents a hydrogen atom, a $C_{1-10}$-alkyl group, an aryl group, an —$NR_aR_b$ group, said $C_{1-10}$-alkyl group and aryl group optionally being substituted with one or more groups selected from hydroxy, $C_{1-6}$-alkyl, $C_{1-6}$-alkoxy, halogen, $CF_3$ or $OCF_3$,
  - it being understood that at least one of $R_1$ or of $R_2$ is different from a hydrogen atom;
  - or alternatively $R_1$ and $R_2$ form, together with the nitrogen atom to which they are attached, a heterocyclic group, said heterocyclic group optionally being substituted with one or more groups selected from hydroxy, $C_{1-6}$-alkyl, $C_{1-6}$-alkylene-O—$C_{1-6}$-alkyl, $C_{1-6}$-alkoxy, halogen, $CF_3$ or $OCF_3$;
- $R_a$ and $R_b$ represent, independently of one another, a hydrogen atom, a $C_{1-6}$-alkyl group, an aryl, $C_{1-6}$-alkylene-aryl or $C_{1-6}$-alkylene-heteroaryl group, said $C_{1-6}$-alkyl, aryl, $C_{1-6}$-alkylene-aryl or $C_{1-6}$-alkylene-heteroaryl group optionally being substituted with one or more groups selected from hydroxy, $C_{1-6}$-alkyl, $C_{1-6}$-alkoxy, halogen, $CF_3$ or $OCF_3$,
  - or alternatively $R_a$ and $R_b$ form, together with the nitrogen atom to which they are attached, a heterocycle, said heterocycle optionally being substituted with one or more groups selected from $C_{1-6}$-alkyl, $C_{1-6}$-alkylene-O—$C_{1-6}$-alkyl or $C_{1-6}$-alkoxy, halogen, $CF_3$ or $OCF_3$;
- $R_3$, joined to the rest of the molecule by one of the two nitrogen atoms of the pyrazolyl, represents a group selected from:
  $C_{1-6}$-alkyl, aryl, $C_{1-6}$-alkylene-aryl or $C_{1-6}$-alkylene-heteroaryl, said alkyl, aryl and heteroaryl groups optionally being substituted with one or more groups selected from a halogen atom, —CN, —$OR_6$, —$NR_6R_7$, —$CONR_6R_7$, —$NR_6COR_7$, or —$COOR_6$, in which:
  $R_6$ and $R_7$ represent, independently of one another, a hydrogen atom, or a $C_{1-6}$-alkyl group;
- $R_4$ and $R_5$ represent, independently of one another, a hydrogen atom, or a $C_{1-6}$-alkyl group,
  - or alternatively $R_4$ and $R_5$ form, together with the carbon atom to which they are attached, a spirocycle containing from 3 to 6 carbon atoms;
  - or alternatively $R_4$ and $R_5$ form together, and with the carbon chain to which they are attached, a saturated ring having 3 or 5 carbon atoms and an oxygen atom, said ring optionally being substituted with one or more groups R, the group or groups R representing, independently of one another, a halogen atom, a $C_{1-3}$-alkyl, or $C_{1-3}$-alkoxy group, or alternatively two groups R, carried by the same carbon atom, together form an oxo group;
- Q represents a hydrogen or halogen atom, a $CF_3$, $OCHF_2$, $OCF_3$, $C_{1-6}$-alkyl, $C_{1-6}$-alkoxy, $C_{3-6}$-cycloalkyl or —O—$C_{3-6}$-cycloalkyl group, said groups optionally being substituted with one or more groups selected from a halogen atom, a hydroxy or $OCF_3$ group,
  - or alternatively Q and $R_5$ form together, and with the carbon chain to which they are attached, a saturated carbon ring having 5 or 6 carbon atoms, said ring optionally being substituted with one or two groups R, the group or groups R representing, independently of one another, groups selected from a halogen atom, $OCHF_2$, $OCF_3$, a $C_{1-3}$-alkyl or $C_{1-3}$-alkoxy group;
  - or alternatively Q and $R_5$ form together, and with the carbon chain to which they are attached, a saturated ring having 4 or 5 carbon atoms and a heteroatom such as O, S or N, said ring and the heteroatom N optionally being substituted with one or more groups R, the group or groups R representing, independently of one another, groups selected from a halogen atom, $OCHF_2$, $OCF_3$, a $C_{1-3}$-alkyl or $C_{1-3}$-alkoxy group, or alternatively two groups R, carried by the same carbon atom, together form an oxo group;
- X and Y represent, independently of one another, a hydrogen atom, a halogen atom, a $C_{1-6}$-alkoxy, —O—$C_{2-6}$-alkenyl, —O-aryl, —O—$C_{1-6}$-alkyl-aryl, —$CF_3$, —$OCF_3$, or $C_{1-6}$-alkyl group;
- V represents a hydrogen atom, a halogen atom, or a $C_{1-4}$-alkyl group;
- n represents an integer selected from 0, 1, 2 or 3
- W represents a hydrogen atom, a halogen atom, $COOR_6$, $CF_3$, $OCHF_2$, $OCF_3$, a $C_{1-6}$-alkyl, $C_{1-6}$-alkoxy, $C_{3-6}$-cycloalkyl heterocycle, —O—$C_{3-6}$-cycloalkyl group, said groups optionally being substituted with one or more groups selected from a halogen atom, a hydroxy, $OCF_3$, or $C_{1-6}$-alkyl group, it being understood that when n is 2 or 3, the two or three groups W represent, independently of one another, the definitions given above.

The compounds of formula (I) can have one or more asymmetric carbon atoms. They can therefore exist in the form of enantiomers or of diastereoisomers. These enantiomers, diastereoisomers, and mixtures thereof, including the racemic mixtures, form part of the invention.

The compounds of formula (I) can be in the form of bases or of salts of addition to acids. Said salts of addition form part of the invention.

These salts are advantageously prepared with pharmaceutically acceptable acids, but the salts of other acids, used for example for the purification or isolation of the compounds of formula (I), also form part of the invention.

The compounds of formula (I) can also be in the form of hydrates and/or of solvates, namely in the form of associations or of combinations with one or more molecules of water and/or of solvent. Said hydrates and solvates also form part of the invention.

The following definitions are used for the purposes of the present invention:

- a halogen atom: a fluorine, a chlorine, a bromine or an iodine;
- a $C_{1-6}$-alkyl group: a saturated, linear or branched monovalent aliphatic group that can comprise 1 to 6 carbon atoms. We may mention, as examples, the methyl, ethyl, propyl, isopropyl, butyl, isobutyl, tert-butyl, pentyl groups; this definition also being valid for the groups $C_{1-3}$-alkyl, $C_{1-4}$-alkyl, $C_{1-10}$-alkyl for example for which only the possible number of carbons changes;
- a $C_{1-6}$-alkylene group: a saturated, linear or branched divalent aliphatic group that can have from 1 to 6 carbon atoms. We may mention, as examples, the methylenyl (—$CH_2$—), ethylenyl (—$CH_2CH_2$—), 1-methylethylenyl (—$CH(CH_3)CH_2$—), propylenyl (—$CH_2CH_2CH_2$—) groups;
- a $C_{1-6}$-alkoxy group: an alkyl-O— radical, where the alkyl group is as defined previously; similarly for the $C_{1-3}$-alkoxy group, for which only the possible number of carbons changes;
- a $C_{2-6}$-alkenyl group: a linear or branched, mono- or polyunsaturated aliphatic group that can comprise from 2 to 6 carbon atoms and for example one or two ethylenic unsaturations. For example, we may mention the groups ethenyl, propenyl;
- a heterocyclic group: a saturated cyclic group with 4 to 7 ring members having one or more heteroatoms such as a nitrogen, oxygen or sulfur atom. We may mention, as examples, the pyrrolidinyl, piperidinyl, tetrahydropyranyl, piperidonyl, morpholinyl, piperazinyl, N-methylpiperazinyl, homomorpholinyl, oxetanyl groups;
- an aryl group is a monocyclic or polycyclic aromatic system having from 6 to 14 carbon atoms, preferably from 6 to 10 carbon atoms. When the system is polycyclic, at least one of the rings is aromatic. We may mention, as examples, the phenyl, naphthyl, tetrahydronaphthyl, indanyl groups;
- a heteroaryl group: a cyclic aromatic group comprising between 1 and 6 carbon atoms and between 1 and 4 heteroatoms, such as nitrogen, oxygen or sulfur. As examples of heteroaromatic groups, we may mention the groups oxazolyl, oxadiazolyl, tetrazolyl, thiazolyl, thiadiazolyl, thienyl, imidazolyl, triazolyl, pyridyl, furanyl, isoxazolyl, pyrrolyl, pyrazolyl, pyrimidinyl, pyridazinyl, and the nitrogen atoms can be, depending on circumstances, in the form of N-oxides;

"two groups R, carried by the same carbon atom, together form an oxo group", the group such as:

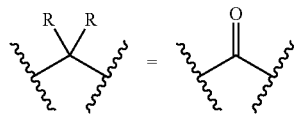

the aromatic group:

is such that one of the carbon atoms of the aromatic ring can be replaced by a nitrogen atom (in the position where there is no substituent W).

"Q and $R_5$ form together, and with the carbon chain to which they are attached, a saturated carbon ring having 5 or 6 carbon atoms", represents a group of the type:

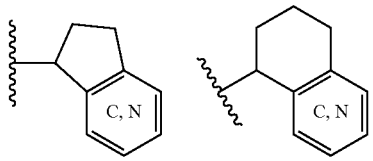

for example.

"Q and $R_5$ form together, and with the carbon chain to which they are attached, a saturated ring having 4 or 5 carbon atoms and a heteroatom", represents a group of the type:

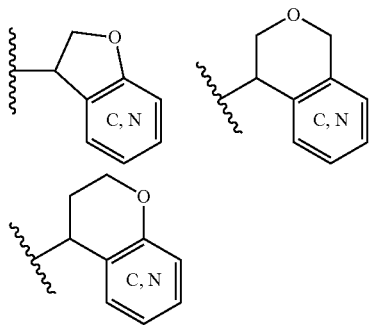

for example.

"$R_4$ and $R_5$ form, together with the carbon atom to which they are attached, a spirocycle containing from 3 to 6 carbon atoms", represents a group of the type:

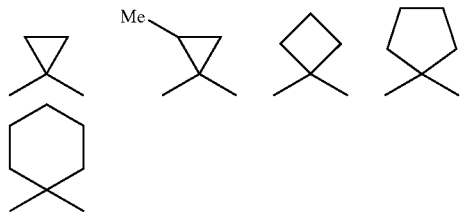

for example.

"R$_4$ and R$_5$ form together, and with the carbon chain to which they are attached, a saturated ring having 3 or 5 carbon atoms and an oxygen atom, said ring optionally being substituted with one or more groups R representing, independently of one another, a halogen atom, a group C$_{1-3}$-alkyl, C$_{1-3}$-alkoxy", represents a group of the type:

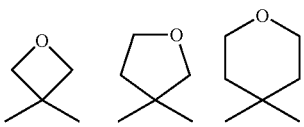

for example

Hereinafter, the nomenclature of the compounds follows IUPAC rules.

Among the compounds of formula (I) according to the invention, a group of compounds is constituted by the compounds of formula (I-bis):

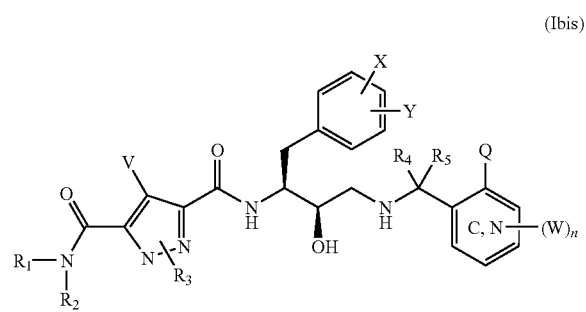

(Ibis)

in which R$_1$, R$_2$, R$_3$, R$_4$, R$_5$, X, Y, n, Q, V and W have the same definitions as the compounds of formula (I).

Among the compounds of formula (I) according to the invention, a group of compounds is constituted by the compounds of formula (I-ter):

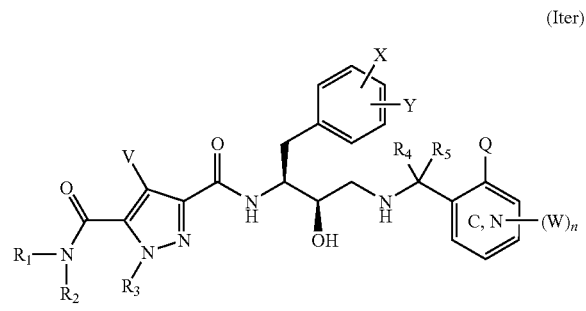

(Iter)

in which R$_1$, R$_2$, R$_3$, R$_4$, R$_5$, X, Y, n, Q, V and W have the same definitions as the compounds of formula (I).

Among the compounds of formula (I) according to the invention, another group of compounds is constituted by the compounds of formula (I-quater):

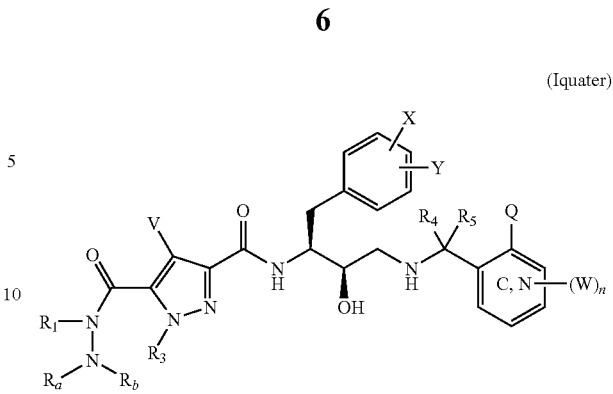

(Iquater)

in which
R$_a$, R$_b$, R$_1$, R$_2$, R$_3$, R$_4$, R$_5$, X, Y, n, Q, V and W have the same definitions as the compounds of formula (I).

Among the compounds according to the invention, other groups of compounds are constituted by the compounds of formulae (I), (I-bis), (I-ter) or (I-quater) for which:

R$_1$ represents a hydrogen atom, a C$_{3-6}$-cycloalkyl group, C$_{1-6}$-alkyl group, said C$_{1-6}$-alkyl optionally being substituted with one or more groups selected from a hydroxy, C$_{1-6}$-alkoxy;

R$_2$ represents a hydrogen atom, a group C$_{1-10}$-alkyl, an aryl, more particularly a phenyl, said C$_{1-10}$-alkyl and phenyl group optionally being substituted with one or more groups selected from hydroxy, C$_{1-6}$-alkyl, C$_{1-6}$-alkoxy;

it being understood that at least one of R$_1$ or of R$_2$ is different from a hydrogen atom;

or R$_2$ represents a group NR$_a$R$_b$ in which:

R$_a$ and R$_b$ represent, independently of one another, a hydrogen atom, a C$_{1-6}$-alkyl group, an aryl, C$_{1-6}$-alkylene-aryl or C$_{1-6}$-alkylene-heteroaryl group, said C$_{1-6}$-alkyl, aryl, C$_{1-6}$-alkylene-aryl or C$_{1-6}$-alkylene-heteroaryl group optionally being substituted with one or more groups selected from hydroxy, C$_{1-6}$-alkyl, C$_{1-6}$-alkoxy, halogen, CF$_3$ or OCF$_3$, Or alternatively R$_a$ and R$_b$ form, together with the nitrogen atom to which they are attached, a heterocycle, said heterocycle optionally being substituted with one or more groups selected from C$_{1-6}$-alkyl, C$_{1-6}$-alkylene-O—C$_{1-6}$-alkyl or C$_{1-6}$-alkoxy, halogen, CF$_3$ or OCF$_3$;

or alternatively R$_1$ and R$_2$ form, together with the nitrogen atom to which they are attached, a heterocyclic group, in particular a piperidinyl or morpholinyl group, said heterocyclic group optionally being substituted with one or more groups selected from C$_{1-6}$-alkyl, C$_{1-6}$-alkoxy, C$_{1-6}$-alkylene-O—C$_{1-6}$-alkyl;

R$_3$ represents a C$_{1-6}$-alkyl group, in particular an ethyl or butyl, or a benzyl group;

R$_4$ and R$_5$ represent, independently of one another, a hydrogen atom, a C$_{1-6}$-alkyl group, or alternatively R$_4$ and R$_5$ form, together with the carbon atom to which they are attached, a spirocycle containing from 3 to 5 carbon atoms; in particular three carbon atoms;

Q represents a hydrogen atom, a C$_{1-3}$-alkyl group;

or alternatively Q and R$_5$ form together, and with the carbon chain to which they are attached, a saturated carbon ring having 5 or 6 carbon atoms, said ring optionally being substituted with one or two groups R, the group or groups R being, independently of one another, selected from a halogen atom, a $C_{1-3}$-alkyl, $OCHF_2$, $OCF_3$, $CF_3$ or $C_{1-3}$-alkoxy group;
or alternatively Q and $R_5$ form together, and with the carbon chain to which they are attached, a saturated ring having 4 or 5 carbon atoms and an oxygen atom, said ring optionally being substituted with one or two groups R, the group or groups R being, independently of one another, selected from a halogen atom, a $C_{1-3}$-alkyl, $OCHF_2$, $OCF_3$, $CF_3$ or $C_{1-3}$-alkoxy group;

X and Y represent, independently of one another, a hydrogen atom, a halogen atom, an —O—$C_{2-6}$-alkenyl, or —O-benzyl group;

n represents an integer selected from 1 or 2;

V represents a hydrogen atom; and

W represents a halogen atom, a $CF_3$, $C_{1-6}$-alkyl, —COOH, $C_{1-6}$-alkoxy group;
it being understood that when n is 2 or 3, the two or three groups W represent, independently of one another, the definitions given above.

Among the compounds according to the invention, other groups of compounds are constituted by the compounds of formulae (I), (I-bis), (I-ter) or (I-quater) for which the carbon bearing $R_4$ is asymmetric and has the following configuration when Q and $R_5$ form together, and with the carbon chain to which they are attached, a ring:

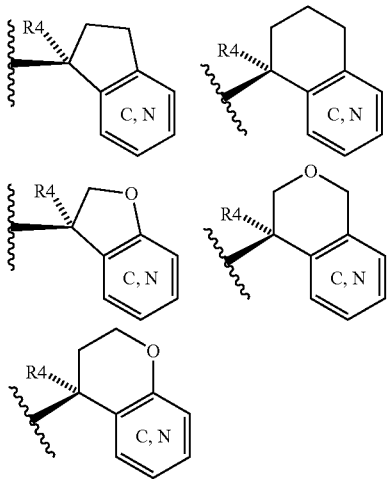

for example.

A group of the invention is also constituted by the compounds of formula (I) in which the groups X and Y are preferably in the meta or para position on the phenyl to which they are attached.

Among the compounds of formula (I) according to the invention, we may notably mention the compounds selected from:

$N^3$-[(1S,2R)-1-benzyl-2-hydroxy-3-{[3-(trifluoromethyl)benzyl]amino}propyl]-1-ethyl-$N^5$,$N^5$-dipropyl-1H-pyrazole-3,5-dicarboxamide;

$N^3$-[(1S,2R)-1-benzyl-2-hydroxy-3-{[3-(methoxy)benzyl]amino}propyl]-1-ethyl-$N^5$,$N^5$-dipropyl-1H-pyrazole-3,5-dicarboxamide;

1-ethyl-$N^3$-[(1S,2R)-2-hydroxy-1-[3-(prop-2-en-1-yloxy)benzyl]-3-({1-[3-(trifluoromethyl)phenyl]cyclopropyl}amino)propyl]-$N^5$,$N^5$-dipropyl-1H-pyrazole-3,5-dicarboxamide;

$N^3$-[(1S,2R)-1-[4-(benzyloxy)benzyl]-2-hydroxy-3-({1-[3-(trifluoromethyl)phenyl]cyclopropyl}amino)propyl]-1-ethyl-$N^5$,$N^5$-dipropyl-1H-pyrazole-3,5-dicarboxamide;

$N^3$-[(1S,2R)-1-(3,5-difluorobenzyl)-2-hydroxy-3-{[3-(trifluoromethyl)benzyl]amino}propyl]-1-ethyl-$N^5$,$N^5$-dipropyl-1H-pyrazole-3,5-dicarboxamide;

1-benzyl-$N^3$-[(1S,2R)-1-benzyl-2-hydroxy-3-{[3-(trifluoromethyl)benzyl]amino}propyl]-$N^5$,$N^5$-dipropyl-1H-pyrazole-3,5-dicarboxamide;

$N^3$-[(1S,2R)-1-benzyl-2-hydroxy-3-{[3-(trifluoromethyl)benzyl]amino}propyl]-$N^5$,$N^5$-dibutyl-1-ethyl-1H-pyrazole-3,5-dicarboxamide;

$N^3$-[(1S,2R)-1-benzyl-2-hydroxy-3-{[3-(trifluoromethyl)benzyl]amino}propyl]-1-ethyl-$N^5$-(1-propylbutyl)-1H-pyrazole-3,5-dicarboxamide;

$N^3$-[(1S,2R)-1-benzyl-2-hydroxy-3-{[3-(trifluoromethyl)benzyl]amino}propyl]-$N^5$-cyclopropyl-1-ethyl-1H-pyrazole-3,5-dicarboxamide;

$N^3$-[(1S,2R)-1-benzyl-2-hydroxy-3-{[3-(trifluoromethyl)benzyl]amino}propyl]-$N^5$-butyl-$N^5$-cyclopropyl-1-ethyl-1H-pyrazole-3,5-dicarboxamide;

$N^3$-[(1S,2R)-1-benzyl-2-hydroxy-3-{[3-(trifluoromethyl)benzyl]amino}propyl]-$N^5$-butyl-1-ethyl-1H-pyrazole-3,5-dicarboxamide;

$N^3$-[(1S,2R)-1-benzyl-2-hydroxy-3-{[3-(trifluoromethyl)benzyl]amino}propyl]-1-ethyl-$N^5$-hexyl-1H-pyrazole-3,5-dicarboxamide;

$N^3$-[(1S,2R)-1-benzyl-2-hydroxy-3-{[3-(trifluoromethyl)benzyl]amino}propyl]-1-ethyl-$N^5$-methyl-$N^5$-pentyl-1H-pyrazole-3,5-dicarboxamide;

$N^3$-[(1S,2R)-1-benzyl-2-hydroxy-3-{[3-(trifluoromethyl)benzyl]amino}propyl]-$N^5$-cyclopropyl-1-ethyl-$N^5$-hexyl-1H-pyrazole-3,5-dicarboxamide;

$N^3$-[(1S,2R)-1-benzyl-2-hydroxy-3-{[3-(trifluoromethyl)benzyl]amino}propyl]-1-ethyl-$N^5$-heptyl-$N^5$-methyl-1H-pyrazole-3,5-dicarboxamide;

$N^3$-[(1S,2R)-1-benzyl-2-hydroxy-3-{[3-(trifluoromethyl)benzyl]amino}propyl]-1-ethyl-$N^5$-hexyl-$N^5$-methyl-1H-pyrazole-3,5-dicarboxamide;

$N^3$-[(1S,2R)-1-(3,5-difluorobenzyl)-2-hydroxy-3-{[(1S)-7-methoxy-1,2,3,4-tetrahydronaphthalen-1-yl]amino}propyl]-1-ethyl-$N^5$-hexyl-$N^5$-methyl-1H-pyrazole-3,5-dicarboxamide;

$N^3$-[(1S,2R)-1-(3,5-difluorobenzyl)-2-hydroxy-3-{[(1S)-7-methoxy-1,2,3,4-tetrahydronaphthalen-1-yl]amino}propyl]-$N^5$-(3-ethoxypropyl)-1-ethyl-$N^5$-methyl-1H-pyrazole-3,5-dicarboxamide $N^5$-cyclopropyl-$N^3$-[(1S,2R)-1-(3,5-difluorobenzyl)-2-hydroxy-3-({1-[3-(trifluoromethyl)phenyl]cyclopropyl}amino)propyl]-1-ethyl-$N^5$-hexyl-1H-pyrazole-3,5-dicarboxamide;

$N^3$-[(1S,2R)-1-(3,5-difluorobenzyl)-2-hydroxy-3-({1-[3-(trifluoromethyl)phenyl]cyclopropyl}amino)propyl]-1-ethyl-$N^5$-heptyl-$N^5$-methyl-1H-pyrazole-3,5-dicarboxamide;

$N^3$-[(1S,2R)-1-(3,5-difluorobenzyl)-2-hydroxy-3-{[(1S)-7-methoxy-1,2,3,4-tetrahydronaphthalen-1-yl]amino}propyl]-1-ethyl-$N^5$-heptyl-$N^5$-methyl-1H-pyrazole-3,5-dicarboxamide;

$N^3$-[(1S,2R)-1-benzyl-2-hydroxy-3-{[3-(trifluoromethyl)benzyl]amino}propyl]-$N^5$-cyclopropyl-1-ethyl-$N^5$-(3-hydroxypropyl)-1H-pyrazole-3,5-dicarboxamide;

$N^3$-[(1S,2R)-1-benzyl-2-hydroxy-3-{[3-(trifluoromethyl)benzyl]amino}propyl]-$N^5$-cyclopropyl-1-ethyl-$N^5$-(4-hydroxybutyl)-1H-pyrazole-3,5-dicarboxamide;

$N^3$-[(1S,2R)-1-benzyl-2-hydroxy-3-{[3-(trifluoromethyl)benzyl]amino}propyl]-$N^5$-cyclopropyl-1-ethyl-$N^5$-(5-hydroxypentyl)-1H-pyrazole-3,5-dicarboxamide;

N³-[(1S,2R)-1-benzyl-2-hydroxy-3-{[3-(trifluoromethyl)benzyl]amino}propyl]-N⁵-cyclopropyl-N⁵-(3-ethoxypropyl)-1-ethyl-1H-pyrazole-3,5-dicarboxamide;

N⁵-cyclopropyl-N³-[(1S,2R)-1-(3,5-difluorobenzyl)-2-hydroxy-3-{[(1S)-7-methoxy-1,2,3,4-tetrahydronaphthalen-1-yl]amino}propyl]-N⁵-(3-ethoxypropyl)-1-ethyl-1H-pyrazole-3,5-dicarboxamide N³-[(1S,2R)-1-benzyl-2-hydroxy-3-{[3-(trifluoromethyl)benzyl]amino}propyl]-1-ethyl-N⁵-(2-ethyl phenyl)-1H-pyrazole-3,5-dicarboxamide;

N³-[(1S,2R)-1-benzyl-2-hydroxy-3-{[3-(trifluoromethyl)benzyl]amino}propyl]-N⁵-butyl-1-ethyl-N⁵-(2-ethylphenyl)-1H-pyrazole-3,5-dicarboxamide;

N-[(1S,2R)-1-benzyl-2-hydroxy-3-{[3-(trifluoromethyl)benzyl]amino}propyl]-1-ethyl-5-(morpholin-4-ylcarbonyl)-1H-pyrazole-3-carboxamide;

N-[(1S,2R)-1-benzyl-2-hydroxy-3-{[3-(trifluoromethyl)benzyl]amino}propyl]-1-ethyl-5-[(5-ethyl-2-methyl piperidin-1-yl)carbonyl]-1H-pyrazole-3-carboxamide;

N-[(1S,2R)-1-benzyl-2-hydroxy-3-{[3-(trifluoromethyl)benzyl]amino}propyl]-1-butyl-5-[(2-propylpiperidin-1-yl)carbonyl]-1H-pyrazole-3-carboxamide;

1-benzyl-N-[(1S,2R)-1-benzyl-2-hydroxy-3-{[3-(trifluoromethyl)benzyl]amino}propyl]-5-[(2-propylpiperidin-1-yl)carbonyl]-1H-pyrazole-3-carboxamide;

N-[(1S,2R)-1-benzyl-2-hydroxy-3-{[3-(trifluoromethyl)benzyl]amino}propyl]-1-ethyl-5-[(2-propyl piperidin-1-yl)carbonyl]-1H-pyrazole-3-carboxamide;

N-[(1S,2R)-1-benzyl-2-hydroxy-3-{[3-(trifluoromethyl)benzyl]amino}propyl]-1-ethyl-5-{[(2S)-2-propylpiperidin-1-yl]carbonyl}-1H-pyrazole-3-carboxamide;

N-[(1S,2R)-1-benzyl-2-hydroxy-3-{[3-(trifluoromethyl)benzyl]amino}propyl]-1-ethyl-5-{[(2R)-2-propylpiperidin-1-yl]carbonyl}-1H-pyrazole-3-carboxamide;

N-[(1S,2R)-1-benzyl-3-(benzylamino)-2-hydroxypropyl]-1-ethyl-5-[(2-propylpiperidin-1-yl)carbonyl]-1H-pyrazole-3-carboxamide;

N-[(1S,2R)-1-benzyl-3-{[4-fluoro-3-(trifluoromethyl)benzyl]amino}-2-hydroxypropyl]-1-ethyl-5[(2-propylpiperidin-1-yl)carbonyl]-1H-pyrazole-3-carboxamide;

N-{(1S,2R)-1-benzyl-3-[(4-fluorobenzyl)amino]-2-hydroxypropyl}-1-ethyl-5-[(2-propylpiperidin-1-yl)carbonyl]-1H-pyrazole-3-carboxamide;

N-{(1S,2R)-1-benzyl-3-[(3,5-difluorobenzyl)amino]-2-hydroxypropyl}-1-ethyl-5-[(2-propylpiperidin-1-yl)carbonyl]-1H-pyrazole-3-carboxamide;

N-{(1S,2R)-1-benzyl-3-[(3-bromobenzyl)amino]-2-hydroxypropyl}-1-ethyl-5-[(2-propylpiperidin-1-yl)carbonyl]-1H-pyrazole-3-carboxamide;

N-{(1S,2R)-1-benzyl-2-hydroxy-3-[(3-methylbenzyl)amino]propyl}-1-ethyl-5-[(2-propylpiperidin-1-yl)carbonyl]-1H-pyrazole-3-carboxamide;

N-{(1S,2R)-1-benzyl-3-[(4-fluoro-3-methylbenzyl)amino]-2-hydroxypropyl}-1-ethyl-5-[(2-propylpiperidin-1-yl)carbonyl]-1H-pyrazole-3-carboxamide;

4-[({(2R,3S)-3-[({1-ethyl-5-[(2-propylpiperidin-1-yl)carbonyl]-1H-pyrazol-3-yl}carbonyl)amino]-2-hydroxy-4-phenylbutyl}amino)methyl]benzoic acid;

N-[(1S,2R)-1-benzyl-3-{[3,5-bis(trifluoromethyl)benzyl]amino}-2-hydroxypropyl]-1-ethyl-5-[(2-propylpiperidin-1-yl)carbonyl]-1H-pyrazole-3-carboxamide;

N-{(1S,2R)-1-benzyl-2-hydroxy-3-[(3-methoxybenzyl)amino]propyl}-1-ethyl-5-[(2-propylpiperidin-1-yl)carbonyl]-1H-pyrazole-3-carboxamide;

N-{(1S,2R)-1-benzyl-2-hydroxy-3-[(pyridin-3-ylmethyl)amino]propyl}-1-ethyl-5-[(2-propylpiperidin-1-yl)carbonyl]-1H-pyrazole-3-carboxamide;

N-[(1S,2R)-1-(3,5-difluorobenzyl)-2-hydroxy-3-{[3-(trifluoromethyl)benzyl]amino}propyl]-1-ethyl-5-[(2-propylpiperidin-1-yl)carbonyl]-1H-pyrazole-3-carboxamide;

N-{(1S,2R)-1-benzyl-2-hydroxy-3-[(1-methyl-1-phenylethyl)amino]propyl}-1-ethyl-5-[(2-propylpiperidin-1-yl)carbonyl]-1H-pyrazole-3-carboxamide;

N-{(1S,2R)-1-benzyl-2-hydroxy-3-({1-methyl-1-[3-(trifluoromethyl)phenyl]ethyl}amino)propyl}-1-ethyl-5-[(2-propylpiperidin-1-yl)carbonyl]-1H-pyrazole-3-carboxamide;

N-{(1S,2R)-1-(3,5-difluorobenzyl)-2-hydroxy-3-({1-methyl-1-[3-(trifluoromethyl)phenyl]ethyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({1-[3-(trifluoromethyl)phenyl]cyclopropyl}amino)propyl}-1-ethyl-5-[(2-propylpiperidin-1-yl)carbonyl]-1H-pyrazole-3-carboxamide;

N-{(1S,2R)-1-[3-(prop-2-en-1-yloxy)benzyl]-2-hydroxy-3-({1-[3-(trifluoromethyl)phenyl]cyclopropyl}amino)propyl}-1-ethyl-5-[(2-propylpiperidin-1-yl)carbonyl]-1H-pyrazole-3-carboxamide;

N-{(1S,2R)-1-(3,5-difluorobenzyl)-2-hydroxy-3-({1-[3-(trifluoromethyl)phenyl]cyclopropyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1R)-1-[3-methoxyphenyl]propyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1R)-1-[3,5-bis(trifluoromethyl)phenyl]ethyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1R)-1-[3-methoxyphenyl]ethyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1R)-1-[3-(trifluoromethyl) phenyl]ethyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-([(1R)-7-methoxy-1,2,3,4-tetrahydronaphthalen-1-yl]amino)propyl}-1-ethyl-5-[(2-propylpiperidin-1-yl)carbonyl]-1H-pyrazole-3-carboxamide;

N-{(1S,2R)-1-benzyl-2-hydroxy-3-([(1R)-6-methoxy-2,3-dihydro-1H-inden-1-yl]amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1S)-1-[3-methoxyphenyl]ethyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-({(1S)-1-[3-methoxyphenyl]propyl}amino)propyl}-1-ethyl-5-[(2-propylpiperidin-1-yl)carbonyl]-1H-pyrazole-3-carboxamide;

N-{(1S,2R)-1-benzyl-2-hydroxy-3-([(1S)-6-methoxy-2,3-dihydro-1H-inden-1-yl]amino)propyl}-1-ethyl-5-[(2-propylpiperidin-1-yl)carbonyl]-1H-pyrazole-3-carboxamide;

N-{(1S,2R)-1-benzyl-2-hydroxy-3-([(1S)-7-methoxy-1,2,3,4-tetrahydronaphthalen-1-yl]amino)propyl}-1-ethyl-5-[(2-propylpiperidin-1-yl)carbonyl]-1H-pyrazole-3-carboxamide;

N-{(1S,2R)-1-(3,5-difluorobenzyl)-2-hydroxy-3-([(1S)-7-methoxy-1,2,3,4-tetrahydronaphthalen-1-yl]amino)propyl}-1-ethyl-5-[(2-propylpiperidin-1-yl)carbonyl]-1H-pyrazole-3-carboxamide;

N-[(1S,2R)-1-(3,5-difluorobenzyl)-2-hydroxy-3-{[(1S)-7-(trifluoromethyl)-1,2,3,4-tetrahydronaphthalen-1-yl]amino}propyl]-1-ethyl-5-[(2-propylpiperidin-1-yl)carbonyl]-1H-pyrazole-3-carboxamide N-[(1S,2R)-1-benzyl-2-hydroxy-3-{[3-(trifluoromethyl)benzyl]amino}propyl]-1-ethyl-5-{[2-(methoxymethyl)piperidin-1-yl]carbonyl}-1H-pyrazole-3-carboxamide;

N-[(1S,2R)-1-(3,5-difluorobenzyl)-2-hydroxy-3-{[3-(trifluoromethyl)benzyl]amino}propyl]-1-ethyl-5-{[2-(methoxymethyl)piperidin-1-yl]carbonyl}-1H-pyrazole-3-carboxamide;

N³-[(1S,2R)-1-benzyl-2-hydroxy-3-{[3-(trifluoromethyl)benzyl]amino}propyl]-N⁵-(2,6-dimethylpiperidin-1-yl)-1-ethyl-1H-pyrazole-3,5-dicarboxamide;

5-[(2-benzyl-2-ethylhydrazino)carbonyl]-N-[(1S,2R)-1-benzyl-2-hydroxy-3-{[3-(trifluoromethyl)benzyl]amino}propyl]-1-ethyl-1H-pyrazole-3-carboxamide;

N³-[(1S,2R)-1-benzyl-2-hydroxy-3-{[3-(trifluoromethyl)benzyl]amino}propyl]-1-ethyl-N⁵-[2-(methoxymethyl)pyrrolidin-1-yl]-1H-pyrazole-3,5-dicarboxamide;

5-[(2-benzyl-2-ethylhydrazino)carbonyl]-N-[(1S,2R)-1-(3,5-difluorobenzyl)-2-hydroxy-3-{[3-(trifluoromethyl)benzyl]amino}propyl]-1-ethyl-1H-pyrazole-3-carboxamide;

N³-[(1S,2R)-1-(3,5-difluorobenzyl)-2-hydroxy-3-{[3-(trifluoromethyl)benzyl]amino}propyl]-1-ethyl-N⁵-[2-(methoxymethyl)pyrrolidin-1-yl]-1H-pyrazole-3,5-dicarboxamide.

The combinations of the groups according to the invention as previously defined also form part of the invention.

In accordance with the invention, the compounds of formula (I) can be prepared according to the method illustrated by Scheme 1 given below.

In the schemes given below, when the method of preparation of the starting compounds and reagents is not described, they are commercially available or are described in the literature, or alternatively can be prepared according to methods that are described in the literature or are known by a person skilled in the art.

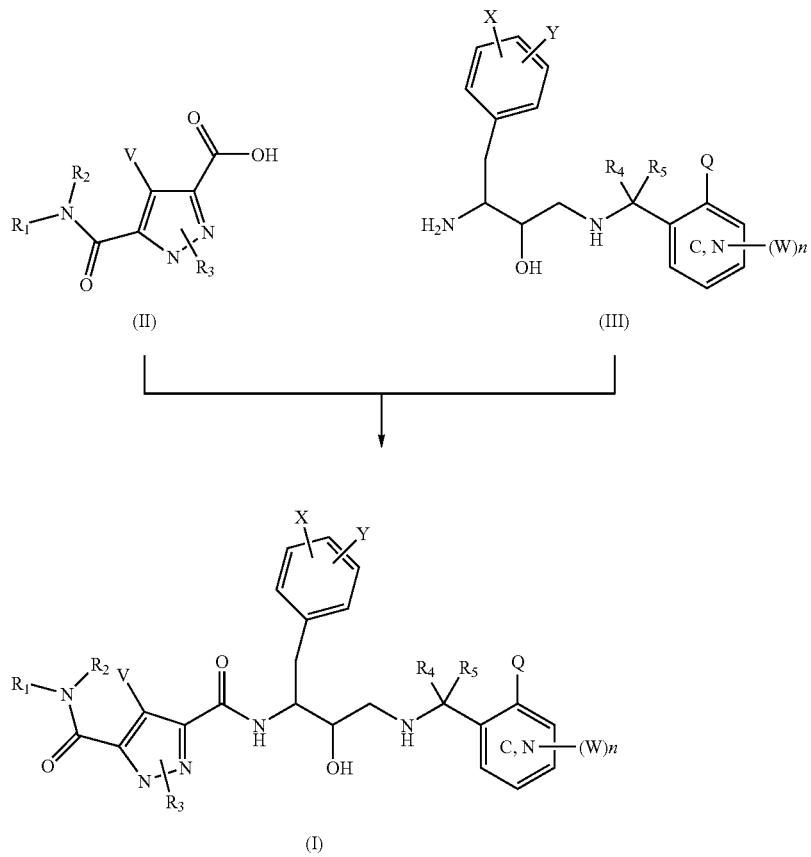

Scheme 1

According to Scheme 1 above, the compound of formula (I) can be obtained by acylation of the amine of formula (III)—in which X, Y, R₄, R₅, Q, W and n are as defined for the compound of formula (I)—with the pyrazole acid of formula (II)—in which R₁, R₂, R₃ and V are as defined for the compound of formula (I)—according to conditions known by a person skilled in the art, for example in the presence of hydroxybenzotriazole hydrate (HOBt) and 1-ethyl-3-(3-dimethylamino-propyl)carbodiimide hydrochloride (EDAC) in an inert solvent such as N,N'-dimethylformamide (DMF), acetonitrile or dichloromethane (DCM) at a temperature that can range from 0° C. to room temperature (B. M. Trost, I. Fleming, E. Winterfeldt, *Comprehensive Organic Synthesis*, 1991, vol. 6, 1st edition, Pergamon Press, Oxford, 381-417). The compound of formula (I) is preferably synthesized from the chiral (2R,3S) amine of formula (III) and in this case the conformation of the final compound of formula (I) is (1S,2R).

Scheme 2
Schéma 2

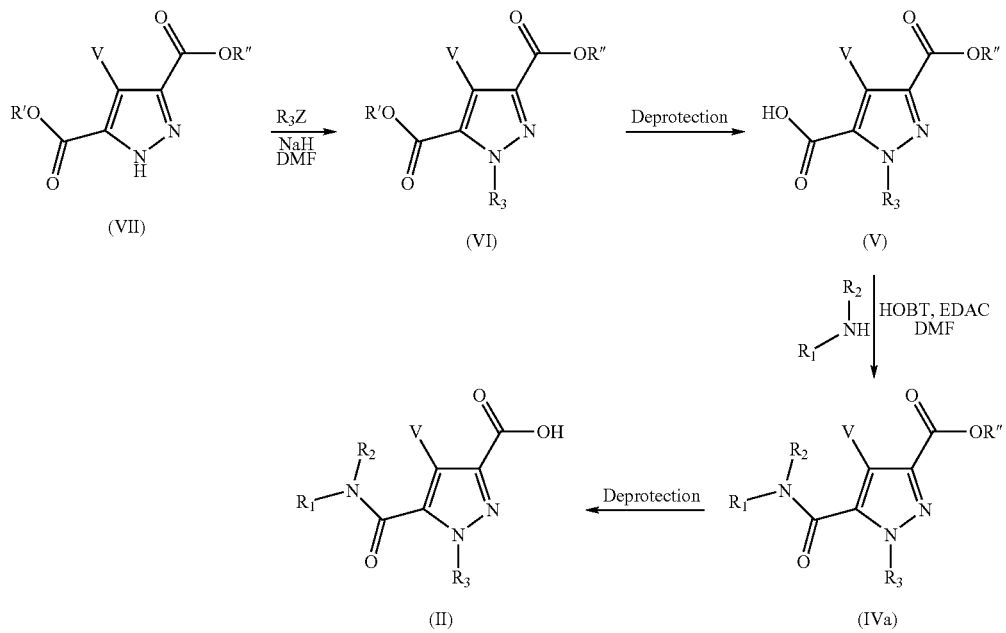

As described in Scheme 2 above, the aforementioned compound of formula (II) can be obtained by a sequence of reactions starting from the dialkyl pyrazole 3,5-dicarboxylate of formula (VII) in which R' and R" can represent, independently of one another, a $C_{1-6}$-alkyl group, in particular methyl, ethyl, tert-butyl, or benzyl. This disubstituted pyrazole of formula (VII) is either commercially available such as 1H-pyrazole-3,5-diethyl dicarboxylate, or is synthesized according to methods known by a person skilled in the art (J. A. Joule, K. Mills, Heterocyclic Chemistry, 2000, 4th edition, Blackwell Science, 448).

More precisely, according to Scheme 2, we obtain the N-substituted pyrazole derivative of formula (VI)—in which $R_3$ and V are as defined for the compound of formula (I)—and R' and R" represent protecting groups of the carboxylic acid functions, for example an ethyl group (T. W. Greene, P. G. M. Wuts Protective Groups in Organic Synthesis, 1999, 3rd Edition, John Wiley and Sons, Inc., 369-431), by reaction of substitution of an NH-pyrazole diester derivative of formula (VII)—in which V, R' and R" are as defined for the compound of formula (VI)—by an alkylating agent of formula $R_3$—Z in which Z is a nucleophilic group known by a person skilled in the art, for example a halide, a mesylate, a tosylate. This reaction is carried out in the presence of a base such as sodium hydride, in an inert solvent such as DMF (S. C. Kuo, L. J. Huang, H. Nakamura, J. Med. Chem; 1984, 49, 539).

When we wish to obtain pyrazole derivatives of formula (VI) in which $R_3$ is an aryl or heteroaryl group, for example the compounds of formula (VII), as described previously, are submitted to a reaction of aromatic nucleophilic substitution or a reaction of the Ullmann type (R. Bambal, R. B. Hazilnik, J. Org. Chem. 1994, 59, 729-732; J. Hassan, M. Sevignon, C. Gozzi, E. Schultz, M. Lemaire, Chem. Rev., 2002, 102, 1359-1470; A. Klapars, J. C. Antilla; X. Huang, S. I. Buchwald, J. Am. Chem. Soc., 2001, 123, 7727-7729).

We obtain the compound of formula (V)—in which $R_3$, V and R" are as defined for the compound of formula (VI)—by selective deprotection in position 5 of the compound of formula (VI) obtained previously, according to methods known by a person skilled in the art (T. W. Greene, P. G. M. Wuts Protective Groups in Organic Synthesis, 1999, 3rd Edition, John Wiley and Sons, Inc., 369-431).

This reaction of selective deprotection can for example be carried out in the presence of lithium hydroxide in a mixture of equal volumes of tetrahydrofuran and distilled water at room temperature, notably in the case when R' and R" are both an ethyl group.

We obtain the monoester derivative of formula (IVa)—in which $R_1$, $R_2$, $R_3$ and V are as defined for the compound of formula (I) and R" is as defined for the compound of formula (V)—by a reaction of acylation of the compound of formula (V)—by $R_1R_2NH$ in which $R_1$ and $R_2$ are as defined for the compound of formula (I)—by an acid derivative of formula (V), as defined previously, according to conditions known by a person skilled in the art, for example in the presence of HOBt and EDAC and in an inert solvent such as DMF (B. M. Trost, I. Fleming, E. Winterfeldt Comprehensive Organic Synthesis, 1991, vol. 6, 1st edition, Pergamon Press, Exeter, 381-417).

Finally we obtain the compound of formula (II) in which $R_1$, $R_2$, $R_3$ and V are as defined for the compound of formula (I), by a reaction of deprotection of the compound of formula (IVa) obtained previously, according to methods known by a person skilled in the art, for example in the presence of lithium hydroxide, in a mixture of equal volumes of THF and distilled water at room temperature, in particular when R" represents an ethyl group.

Alternatively, the compounds of formula (II) in which $R_3$ is an alkyl can be obtained from the derivative of formula (IVa) in which $R_3$ is a benzyl, the other groups being as defined previously.

In this case, the derivative of formula (IVa) is debenzylated according to the conditions of deprotection known by a person skilled in the art, for example in the presence of ammonium formate and 10% Pd/C in absolute ethanol (T. W.

Greene, P. G. M. Wuts Protective Groups in Organic Synthesis, 1999, 3rd Edition, John Wiley and Sons, Inc., 578-580).

The N-debenzylated amide thus obtained then undergoes a reaction of alkylation following the conditions known by a person skilled in the art, such as those used for the synthesis of the compound of formula (VI), which can give the 2 possible regioisomers, which are then deprotected in acids.

Alternatively, we can obtain the compositions of formula (IVa), so that the compound of formula (II) can be obtained according to the following Scheme 3.

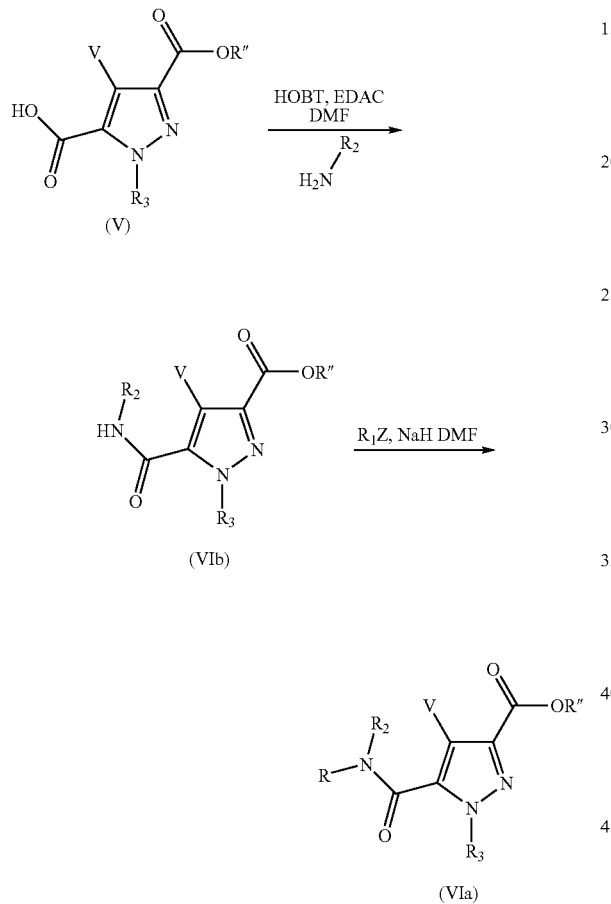

Thus, the compounds of formula (IVa) as defined previously are obtained by a reaction of N-alkylation on the compound of formula (IVb)—in which $R_2$, $R_3$, V and R" are as defined for the compound of formula (IVa)—according to the methods known by a person skilled in the art (R. C. Larock Comprehensive Organic Transformations, 1999, $2^{nd}$ Edition, John Wiley & Sons, Inc., New York, 1979-1980), by an alkylating agent for example of formula $R_1$—Z in which $R_1$ is as defined for the compound of formula (I) (except for a hydrogen) and Z is as defined previously.

We obtain the compound of formula (IVb) by a reaction of acylation of the compound of formula $R_2$—$NH_2$ by the acid derivative of formula (V) as defined previously, according to the conditions known by a person skilled in the art, for example in the presence of HOBt and EDAC in an inert solvent such as DMF (B. M. Trost, I. Fleming, E. Winterfeldt Comprehensive Organic Synthesis, 1991, vol. 6, 1st edition, Pergamon Press, Exeter, 381-417).

The amine derivatives of formula (III) can be obtained according to Scheme 4 given below.

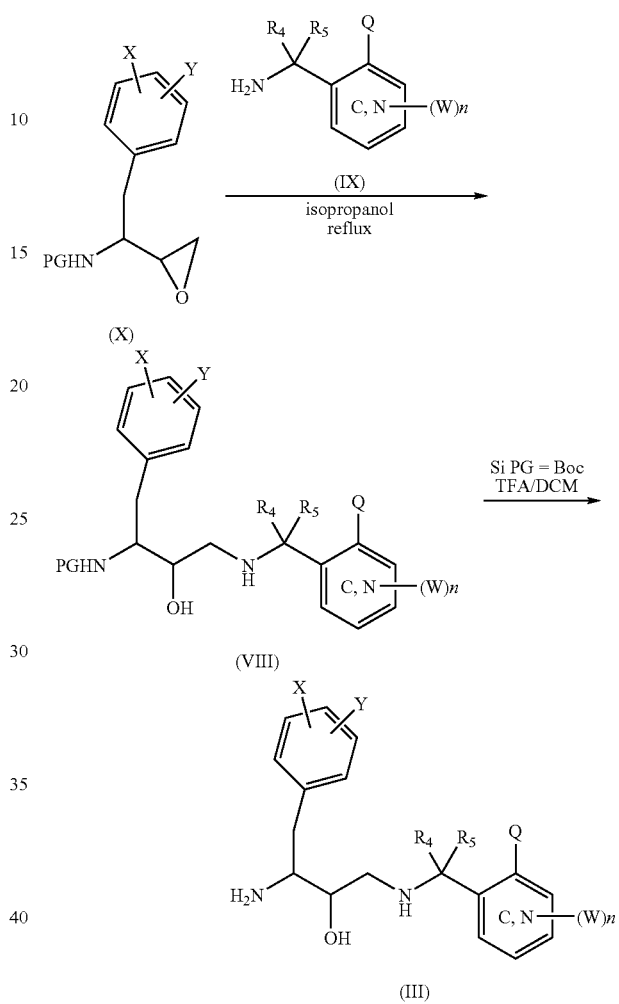

We obtain the compounds of formula (III)—in which $R_4$, $R_5$, X, Y, Q, W and n are as defined for the compound of formula (I)—by a reaction of deprotection of the amine derivative of formula (VIII)—in which $R_4$, $R_5$, X, Y, Q, W and n are as defined for the compound of formula (I) and PG represents a protecting group (T. W. Greene, P. G. M. Wuts Protective Groups in Organic Synthesis, 1999, 3rd Edition, John Wiley and Sons, Inc., 369-431).

For example, if the protecting group is a tert-butoxycarbonyl (Boc), the amine derivative of formula (VIII) is treated with trifluoroacetic acid in dichloromethane (mixture of equal volumes).

We obtain the compound of formula (VIII) as defined previously, by reaction of the compound of formula (X)—in which X and Y are as defined for the compound of formula (I) and PG represents a protecting group—with a compound of formula (IX)—in which R4, R5, Q, W and n are as defined for the compound of formula (I)—according to the conditions known by a person skilled in the art, for example in isopropanol under reflux (A. K. Gosh, S. Leshchenko, M. Noetzel J. Org. Chem., 2004, 69, 7822-7829) or in dichloroethane (DCE) heated between 40° C. and 85° C. in the presence of a catalytic amount of lithium trifluoromethane sulfonimide (J. Cossy, V. Bellosta, C. Hamoir, J.-R. Desmurs Tetrahedron Lett., 2002, 43, 7083-7086).

The compound of formula (IX) is either commercially available or is synthesized from commercial compounds and according to methods known by a person skilled in the art (E. Ciganek J. Org. Chem., 1992, 57, 4521-4527; P. Bertus, J. Szymoniak, J. Org. Chem., 2003, 68, 7133-7136; T. T. Colyer, N. G. Andersen, J. S. Tedrow, T. S. Soukup, M. M. Faul, J. Org. Chem., 2006, 71, 6859-6862).

The compound of formula (X) is either commercially available or is synthesized according to methods known by a person skilled in the art (R. Luly, J. F. Dellaria, J. J. Plattner, J. L. Soderquist, N. Yi, J. Org. Chem., 1987, 52, 1487).

Preferably, the amine derivative of formula (III) in enantiomeric form (S,R) is obtained from the chiral (S,S) compound of formula (X).

When a function of a compound is reactive, for example when $R_1$ bears a hydroxy, it may require a protection prior to reaction. A person skilled in the art will easily be able to determine whether prior protection is necessary (T. W. Greene, P. G. M. Wuts Protective Groups in Organic Synthesis, 1999, 3rd Edition, John Wiley and Sons, Inc., 369-431).

The methods of synthesis of the various intermediates for obtaining the compounds of the invention are described in the preparations. When these syntheses are not described, the intermediates are either known, or are prepared according to methods that are well known by a person skilled in the art.

The abbreviations and symbols used for describing the synthesis procedures and for naming the compounds are as follows:
DMF for dimethylformamide,
DMSO for dimethylsulfoxide,
THF for tetrahydrofuran,
AcOEt for ethyl acetate
$CH_3CN$ for acetonitrile
$Et_2O$ for diethyl ether
MeOH for methanol
DCM for dichloromethane
HCl for hydrochloric acid,
LiOH for lithium hydroxide,
TFA for trifluoroacetic acid
HOBT for hydroxybenzotriazole hydrate
EDAC for 1-ethyl-3-(3-dimethylaminopropyl)carbodiimide hydrochloride
NaH for sodium hydride
35-10% Pd/C for 10% of palladium on charcoal
Boc for tert-butoxycarbonyl
Et for ethyl,
Me for methyl.

The chiral compounds 34 and 35 are obtained by preparative chiral High Pressure Liquid Chromatography (HPLC) of compound 33. The separation is performed on an HPLC Waters Prep 4000 with a chiral stationary phase, Chiralcel OD-CSP, and the compounds are eluted with a mixture of isohexane and isopropanol (95/5, v/v) containing 0.5% of isopropylamine at 25° C. Detection is performed at 230 nm and the flow rate used is 120 ml/min. The isomeric purity of each chiral compound is determined on a Berger analytical SFC with Chiralcel OD-H stationary phase (250×4.6 mm, 5 μm) and as eluent a mixture of carbon dioxide and isopropanol (87/13) containing 0.5% of isopropylamine. The exact stereochemistry at the level of the coniine amide of compounds 34 and 35 has not been determined.

The proton nuclear magnetic resonance ($^1$H NMR) spectra were obtained at 300 MHz, 500 MHz or 600 MHz on Bruker equipment. The abbreviations used for characterizing the signals are as follows: s=singlet, bs=broad singlet, m=multiplet, d=doublet, dd=doublet of doublet, t=triplet, q=quadruplet.

LC-MS (Liquid Chromatography/Mass Spectrometry) is carried out with a Waters LC-MS ZMD system equipped with an Alliance 2695 and a Waters 996 diode-array UV detector (200 to 400 nm) operated with MassLynx V4.1 software at 40° C. The column used is a Kromasil C18 (50×2 mm, 3.5 μm, 100 ÅAIT) and a mixture of distilled water containing 0.05% TFA and of acetonitrile containing 0.035% TFA (2% to 100% $CH_3CN$+0.035% TFA in 10 min).

The salts and solvates are quantified by means of elementary analysis, determination of water by the Karl Fischer technique and integration of the characteristic signals of the solvents in $^1$H NMR.

Synthesis of the Intermediates of Formulae (II) and (III)

Intermediate 1 of Formula (II)

synthesis of 1-ethyl-5-[(2-propylpiperidin-1-yl)carbonyl]-1H-pyrazole-3-carboxylic acid

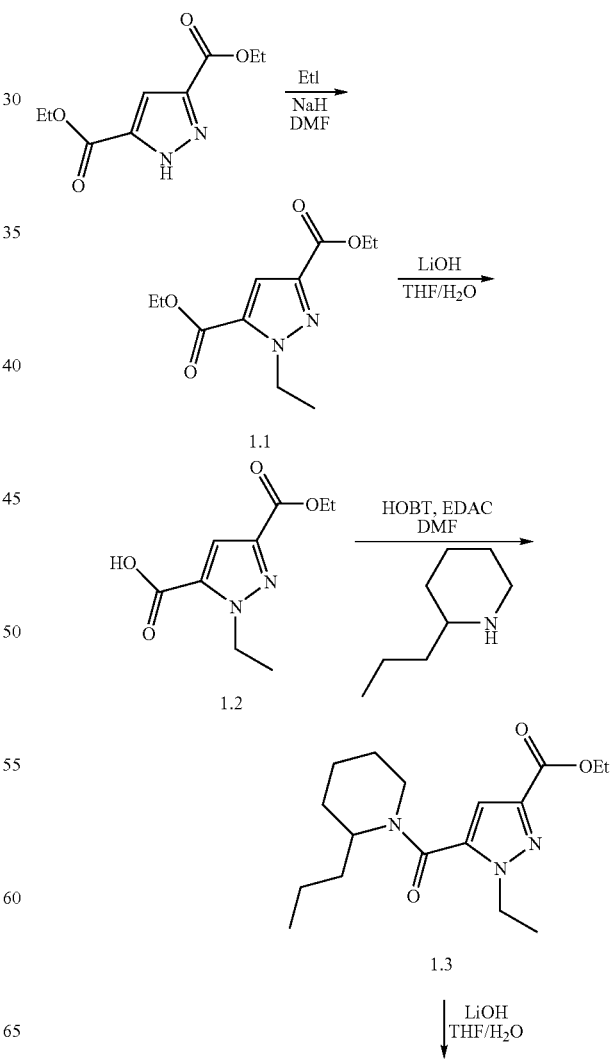

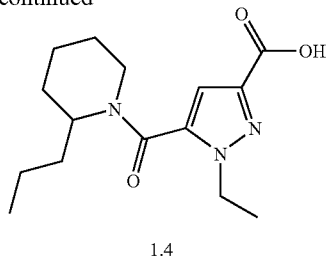

1.4

1.1/ 1-ethyl-1H-pyrazole-3,5-diethyl dicarboxylate

After washing 3.11 g of sodium hydride with pentane, add 5 ml of DMF. Add 1H-pyrazole-3,5-diethyl dicarboxylate, dissolved beforehand in 120 ml of DMF, dropwise at room temperature. Stir the reaction mixture thus obtained for 2 h30 at this temperature and then add ethyl iodide, dissolved beforehand in 60 ml of DMF. After adding the ethyl iodide, continue stirring for 15 h, after which the reaction mixture is evaporated to dryness. The residue obtained is taken up in AcOEt and the organic phase is then washed twice with distilled water, dried over anhydrous sodium sulfate and concentrated under vacuum. The residue obtained is chromatographed on a silica gel column, eluting with a mixture of AcOEt and petroleum ether 1/9 (v/v) and the title product is obtained in the form of yellow oil (14.40 g).

$^1$H NMR (300 MHz, CDCl$_3$) δ ppm: 1.40 (m, 6H), 4.36 (q, 4H), 4.65 (q, 2H), 7.31 (s, 1H).

1.2/ 3-(ethoxycarbonyl)-1-ethyl-1H-pyrazole-5-carboxylic acid

Add 1.24 g of lithium hydroxide to a solution of the diester 1.1 (7.46 g) previously prepared in 350 ml of mixture of THF and distilled water 1/1 (v/v) at room temperature. After stirring for 1 h, the pH is adjusted to 2 and the reaction mixture is extracted with AcOEt. The combined organic phases are washed with distilled water, then dried over anhydrous sodium sulfate and concentrated under vacuum. The residue obtained is chromatographed on a silica gel column, eluting with a gradient of DCM and isopropanol containing 10 vol. % of acetic acid (gradient from 0 to 5% isopropanol+10% AcOH) and the title product is isolated in the form of a white solid (4.69 g).

$^1$H NMR (300 MHz, CDCl$_3$) δ ppm: 1.42 (t, 3H), 1.51 (t, 3H), 4.45 (q, 2H), 4.72 (q, 2H), 7.50 (s, 1H), 10.15 (bs, 1H).

1.3/ 1-ethyl-5-[(2-propylpiperidin-1-yl)carbonyl]-1H-pyrazole-3-ethyl carboxylate Add 5.56 g of HOBt hydrate and 6.96 g of EDAC to a solution of monoacid 1.2 (7.00 g) previously prepared in 140 ml of DMF at room temperature, and continue stirring the solution obtained for 10 min. Then add 3.99 g of racemic coniine and stir the reaction mixture for 15 h. The solvent is evaporated to dryness and the residue is taken up in AcOEt, then it is washed twice with a saturated solution of sodium bicarbonate and once with distilled water. The organic phase is dried over anhydrous sodium sulfate and concentrated under vacuum. The residue obtained is chromatographed on a silica gel column, eluting with a gradient of petroleum ether and AcOEt (gradient from 0 to 20% AcOEt) and the title product is obtained in the form of a colorless oil (5.63 g).

$^1$H NMR (300 MHz, CDCl$_3$) δ ppm: 0.7-0.9 (m, 3H), 1.05-1.9 (m, 16H), 2.8-3.2 (m, 1H), 3.6-4.1 (m, 1H), 4.35 (m, 4H), 4.40-4.90 (m, 1H), 6.74 (s, 1H).

1.4/ 1-ethyl-5-[(2-propylpiperidin-1-yl)carbonyl]-1H-pyrazole-3-carboxylic acid Add 0.57 g of lithium hydroxide to a solution of the ester 1.3 (2.21 g) previously prepared in 50 ml of mixture of THF and distilled water 1/1 (v/v) at room temperature. After stirring for 4 h30, the solvent is evaporated and the residue is taken up in distilled water and AcOEt. The pH is adjusted to 2 and then the reaction mixture is extracted with AcOEt. The combined organic phases are washed with distilled water, dried over anhydrous sodium sulfate and concentrated under vacuum: the title product is isolated in the form of a colorless oil (1.91 g).

$^1$H NMR (300 MHz, CDCl$_3$) δ ppm: 0.75-1.05 (m, 3H), 1.05-1.9 (m, 13H), 2.7-3.2 (m, 1H), 3.6-4.1 (m, 1H), 4.35 (m, 2H), 4.45-4.95 (m, 1H), 6.80 (s, 1H).

Intermediate 2 of Formula (II)

synthesis of 5-(dipropylcarbamoyl)-1-ethyl-1H-pyrazole-3-carboxylic acid

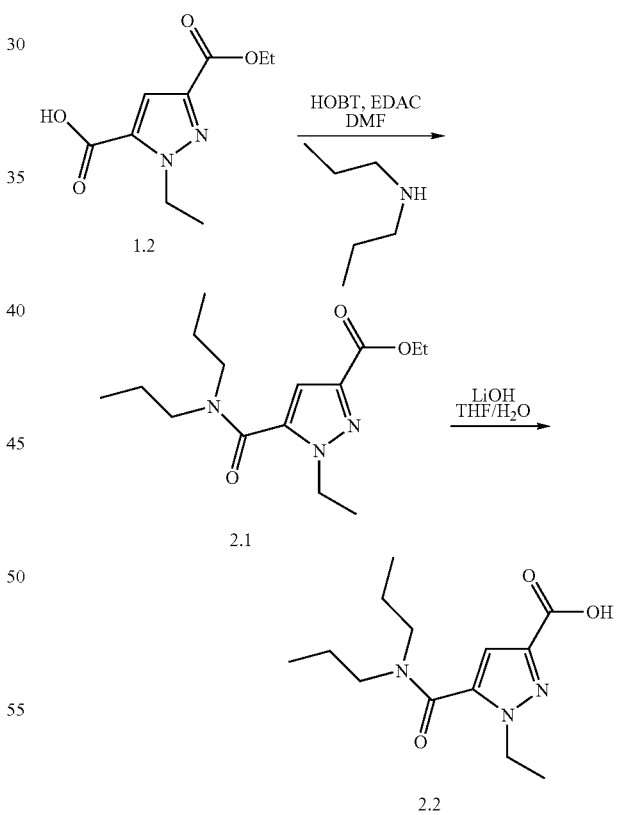

2.1/ 5-(dipropylcarbamoyl)-1-ethyl-1H-pyrazole-3-ethyl carboxylate

Add 11.04 g of HOBt and 13.64 g of EDAC to a solution of monoacid 1.2 (15.00 g) in 300 ml of DMF at room temperature, and stir the solution obtained for 10 min. Then add 2.30 g of dipropylamine and stir the reaction mixture for 15 h. The solvent is evaporated to dryness and the residue is taken up in AcOEt, then washed twice with a saturated solution of sodium bicarbonate and once with distilled water. The organic phase is dried over anhydrous sodium sulfate and concentrated under vacuum. The title product is isolated in the form of a colorless oil (19.00 g).

LCMS: MH$^+$=296

2.2/ 5-(dipropylcarbamoyl)-1-ethyl-1H-pyrazole-3-carboxylic acid

Add 1.52 g of lithium hydroxide to a solution of ester 2.1 (7.00 g) in 300 ml of mixture of THF and distilled water 7/3 (v/v) at room temperature, and heat the reaction mixture at 60° C. for 1 h30. The pH is adjusted to 2 and the reaction mixture is extracted with AcOEt. The combined organic phases are dried over anhydrous sodium sulfate and concentrated under vacuum: the title product is obtained in the form of a white solid (5.2 g).

LCMS: MH$^+$=268

Intermediate 3 of Formula (II)

synthesis of 5-[(2-benzyl-2-ethylhydrazino)carbonyl]-1-ethyl-1H-pyrazole-3-carboxylic acid stir the solution obtained for 10 min. Then add 0.78 g of N-benzyl-N-ethyl-hydrazine and stir the reaction mixture for 15 h. The solvent is evaporated to dryness and the residue is taken up in AcOEt, then washed twice with a saturated solution of sodium bicarbonate and once with distilled water. The organic phase is dried over anhydrous sodium sulfate and concentrated under vacuum. The residue obtained is chromatographed on a silica gel column, eluting with a gradient of petroleum ether and AcOEt (gradient from 0 to 25% AcOEt) and the title product is obtained in the form of a colorless oil (1.53 g).

$^1$H NMR (300 MHz, CDCl$_3$) δ ppm: 0.8 (m, 3H), 1.08-1.38 (m, 6H), 2.91 (m, 2H), 4.03 (m, 2H), 4.32 (m, 2H), 4.48 (m, 2H), 6.80 (s, 1H), 7.25 (m, 5H).

3.2/ 5-[(2-benzyl-2-ethylhydrazino)carbonyl]-1-ethyl-1H-pyrazole-3-carboxylic acid Add 0.37 g of LiOH to a solution of ester 3.1 (1.53 g) in 40 ml of mixture of THF and distilled water 1/1 (v/v) at room temperature. After stirring for 3 h30, the pH is adjusted to a value in the range from 6 to 7 and the reaction mixture is extracted with AcOEt. The combined organic phases are washed with distilled water, dried over anhydrous sodium sulfate and concentrated under vacuum: the title product is obtained in the form of a white solid (0.59 g).

$^1$H NMR (300 MHz, CDCl$_3$) δ ppm: 0.82 (m, 3H), 1.45 (t, 3H), 3.39 (m, 2H), 4.37 (m, 2H), 4.69 (q, 2H), 7.09 (s, 1H), 7.22 (m, 5H).

Intermediate 4 of Formula (III)

synthesis of (2R,3S)-3-amino-4-phenyl-1-{[3-(trifluoromethyl)benzyl]-amino}butan-2-ol

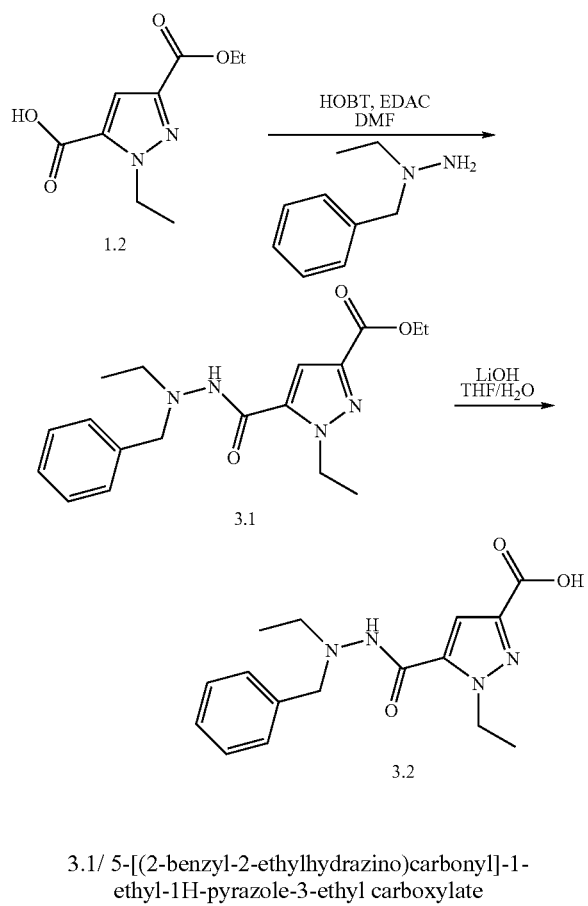

3.1/ 5-[(2-benzyl-2-ethylhydrazino)carbonyl]-1-ethyl-1H-pyrazole-3-ethyl carboxylate Add 0.79 g of HOBt and 0.99 g of EDAC to a solution of monoacid 1.2 (1.00 g) in ml of DMF at room temperature, and

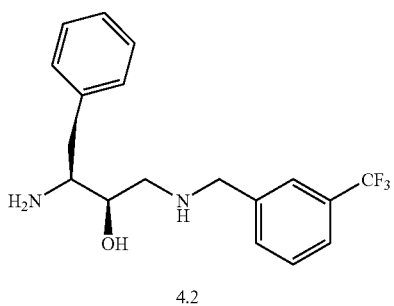

4.2

4.1/ [(1S,2R)-1-benzyl-2-hydroxy-3-{[3-(trifluoromethyl)benzyl]amino}propyl]tert-butyl carbamate Dissolve 3.97 g of the epoxide (S,S) and 3.43 g of 3-trifluoromethylbenzylamine in 151 ml of isopropanol at room temperature. The reaction mixture is then heated under reflux for 15 h. Once at room temperature, a precipitate forms and is therefore filtered: the title product is thus isolated in the form of a white solid (2.69 g).

LCMS: MH$^+$=439

4.2/ (2R,3S)-3-amino-4-phenyl-1-{[3-(trifluoromethyl)benzyl]amino}butan-2-ol Dissolve 2.50 g of the protected amine 4.1, obtained previously, in 7 ml of DCM, and add 7 ml of TFA. The reaction mixture is stirred for 1 h at room temperature, and is then made basic with a saturated solution of sodium bicarbonate. This two-phase mixture is extracted with DCM, and the organic phase is dried over anhydrous sodium sulfate and concentrated under vacuum. The residue obtained is chromatographed on a silica gel column, eluting with a gradient of DCM and methanol (gradient from 0 to 5% MeOH) and the title product is obtained in the form of a colorless oil (1.74 g).

LCMS: MH$^+$=339

Intermediate 5 of Formula (III)

synthesis of (2R,3S)-3-amino-4-(3,5-difluorophenyl)-1-{[3-(trifluoromethyl)benzyl]amino}butan-2-ol

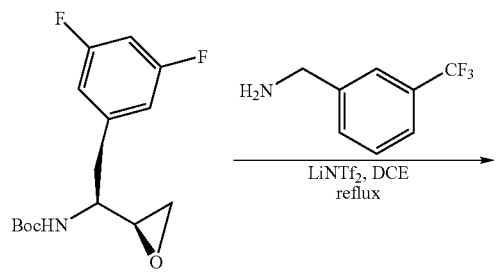

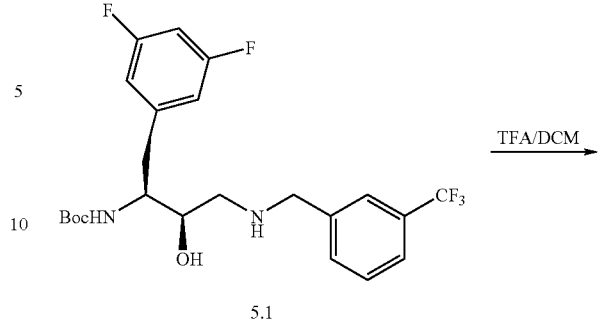

5.1

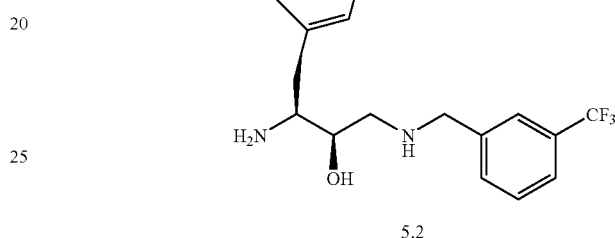

5.2

5.1/ [(1S,2R)-1-(3,5-difluorobenzyl)-2-hydroxy-3-{[3-(trifluoromethyl)benzyl]amino}propyl]tert-butyl carbamate Dissolve 2.00 g of the epoxide (S,S) and 1.41 g of 3-trifluoromethylbenzylamine in 50 ml of dichloroethane (DCE) at room temperature, then add 0.19 g of lithium trifluoromethanesulfonimide. The reaction mixture is then heated at 50° C. for 64 h. Once at room temperature, the solution is washed with distilled water, and the organic phase is dried over anhydrous sodium sulfate and concentrated under vacuum. The residue obtained is chromatographed on a silica gel column, eluting with a gradient of DCM and methanol (gradient from 0 to 5% MeOH) and the title product is obtained in the form of a colorless oil (2.39 g).

NMR (300 MHz, CDCl$_3$) δ ppm: 1.38 (s, 9H), 1.80 (bs, 1H), 2.79 (m, 3H), 3.00 (dd, 1H), 3.49 (m, 1H), 3.87 (m, 3H), 4.61 (d, 1H), 6.71 (m, 3H), 7.52 (m, 4H).

5.2/ (2R,3S)-3-amino-4-(3,5-difluorophenyl)-1-{[3-(trifluoromethyl)-benzyl]amino}butan-2-ol Dissolve 2.39 g of the protected amine 5.1, obtained previously, in 15 ml of DCM, and add 15 ml of TFA. The reaction mixture is stirred for 1 h at room temperature, then evaporated to dryness. The residue is taken up with AcOEt and the solution obtained is washed with a saturated solution of sodium carbonate, and then with distilled water. The organic phase is dried over anhydrous sodium sulfate and concentrated under vacuum. The residue obtained is chromatographed on a silica gel column, eluting with a gradient of DCM and methanol containing 10 vol. % of ammonium hydroxide (gradient from 0 to 5% MeOH+10% NH$_4$OH) and the title product is obtained in the form of a colorless oil (1.66 g).

NMR (300 MHz, CDCl$_3$) δ ppm: 2.51 (m, 1H), 2.77 (m, 1H), 2.92 (m, 2H), 3.13 (m, 1H), 3.60 (m, 1H), 3.91 (d, 2H), 6.73 (m, 3H), 7.53 (m, 4H).

Intermediate 6 of Formula (III)

synthesis of (2R,3S)-3-amino-4-(3,5-difluorophenyl)-1-{[(1S)-5-(trifluoromethyl)-1,2,3,4-tetrahydronaphthalen-1-yl]amino}butan-2-ol

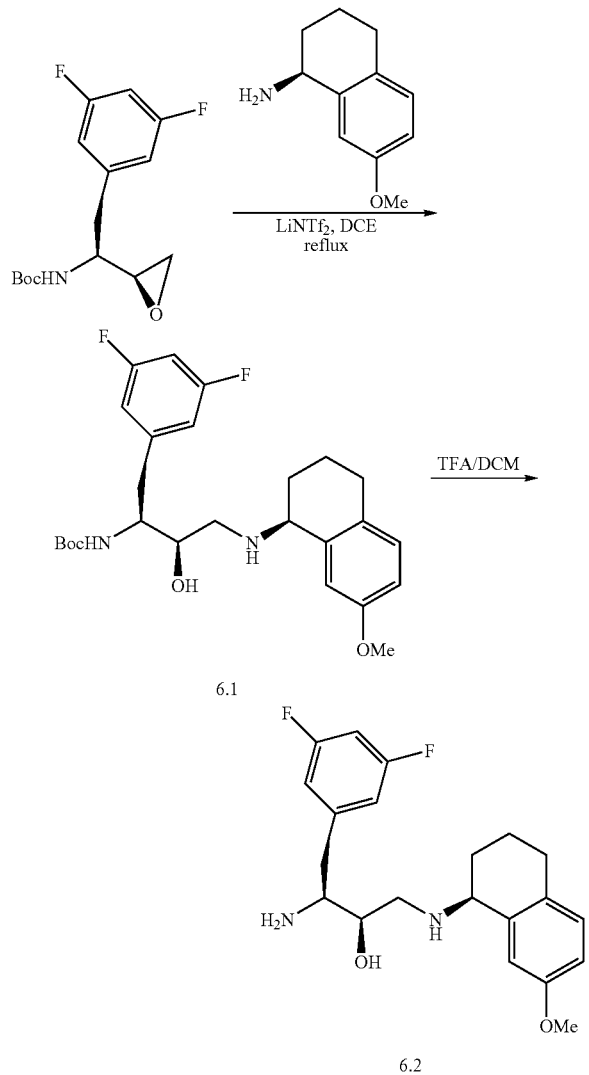

6.1/ [(1S,2R)-1-(3,5-difluorobenzyl)-2-hydroxy-3-{[(1S)-5-(trifluoromethyl)-1,2,3,4-tetrahydronaphthalen-1-yl]amino}propyl]tert-butyl carbamate Dissolve 0.40 g of the epoxide (S,S) and 0.34 g of 7-methoxy-1,2,3,4-tetrahydronaphthylamine hydrochloride in 10 ml of DCE at room temperature, then add 0.04 g of LiNTf$_2$. The reaction mixture is stirred at room temperature for 15 h and then heated at 50° C. for 39 h30. The reaction mixture is concentrated to dryness, and the residue is taken up in AcOEt, then washed with distilled water. The organic phase is dried over anhydrous sodium sulfate and concentrated under vacuum. The residue obtained is chromatographed on a silica gel column, eluting with a gradient of DCM and methanol (gradient from 0 to 3% MeOH) and the title product is obtained in the form of a white solid (0.49 g).

LCMS: MH$^+$=477

6.2/ (2R,3S)-3-amino-4-(3,5-difluorophenyl)-1-{[(1S)-5-(trifluoromethyl)-1,2,3,4-tetrahydronaphthalen-1-yl]amino}butan-2-ol Dissolve 2.15 g of the protected amine 6.1, obtained previously, in 10 ml of DCM, and add 10 ml of TFA. The reaction mixture is stirred for 40 min at room temperature, then evaporated to dryness. The residue is taken up with AcOEt and the solution obtained is washed with a saturated solution of sodium carbonate, and then with distilled water. The organic phase is dried over anhydrous sodium sulfate and concentrated under vacuum. The residue obtained is chromatographed on a silica gel column, eluting with a gradient of DCM and methanol containing 10 vol. % of ammonium hydroxide (gradient from 0 to 6% MeOH+10% NH$_4$OH) and the title product is obtained in the form of a colorless oil (1.44 g).

NMR (300 MHz, CDCl$_3$) δ ppm: 1.92 (m, 3H), 2.17 (m, 3H), 2.52 (m, 1H), 2.73 (m, 1H), 2.84 (m, 1H), 2.95-3.15 (m, 3H), 3.56 (m, 1H), 3.82 (s, 3H), 6.67-6.80 (m, 4H), 6.94 (d, 1H), 7.04 (d, 1H)

The following examples describe the preparation of some compounds according to the invention. These examples are not limiting and only serve to illustrate the invention.

The numbers of the compounds in the examples refer to those given in the table presented later. Elementary microanalyses and NMR, IR or LC-MS (liquid chromatography combined with mass spectrometry) analyses confirm the structures of the compounds obtained.

EXAMPLES OF PREPARATION OF COMPOUNDS OF GENERAL FORMULA (I)

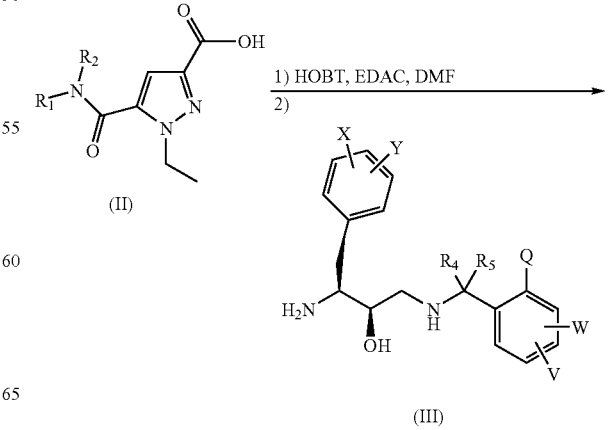

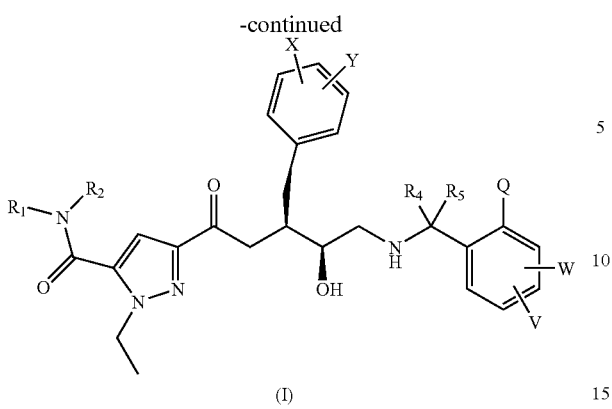

(I)

Example 1

N³-[(1S,2R)-1-(3,5-difluorobenzyl)-2-hydroxy-3-{[3-(trifluoromethyl)-benzyl]amino}propyl]-1-ethyl-N⁵,N⁵-dipropyl-1H-pyrazole-3,5-dicarboxamide (compound 5, Table I)

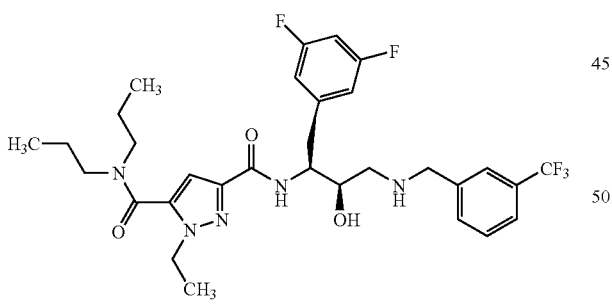

Add 0.09 g of HOBt and 0.12 g of EDAC to a solution of 0.15 g of the acid of formula (II) 2.2 in 8 ml of DMF at room temperature. Stir the solution obtained for 10 min and then add 0.23 g of the amine of formula (III) 5.2. The reaction mixture is stirred for 72 h. The solvent is evaporated to dryness and the residue is taken up in AcOEt, then washed twice with a saturated solution of sodium bicarbonate and once with distilled water. The organic phase is dried over anhydrous sodium sulfate and concentrated under vacuum. The residue obtained is chromatographed on a silica gel column, eluting with a gradient of DCM and methanol (0 to 5% MeOH) and the aminoalcohol is isolated in the form of a base. After dissolving in diethyl ether (Et₂O), a solution of 1N hydrochloric acid in Et₂O is added in order to form the amine hydrochloride. This salt is finally recrystallized from a mixture of DCM, Et₂O and pentane, and 0.26 g of the hydrochloride of product 1 is thus isolated.

LCMS: MH⁺=624
¹H NMR (600 MHz, DMSO-d₆) δ ppm: see Table I.

Example 2

5-[(2-benzyl-2-ethylhydrazino)carbonyl]-N-[(1S,2R)-1-benzyl-2-hydroxy-3-{[3-(trifluoromethyl)benzyl]amino}propyl]-1-ethyl-1H-pyrazole-3-carboxamide (compound 69, Table II)

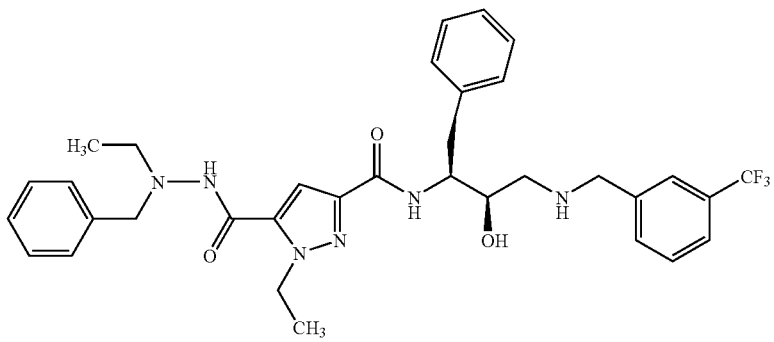 [SMILES: CCN(Cc1ccccc1)NC(=O)c1cc(C(=O)N[C@@H](Cc2ccccc2)[C@H](O)CNCc2cccc(C(F)(F)F)c2)nn1CC]

Following the same procedure as for product 1 and using 0.18 g of the acid of formula (II) 3.2, 0.10 g of HOBt, 0.12 g of EDAC and 0.21 g of amine of formula (III) 4.2 in 7 ml of DMF, 0.23 g of the hydrochloride of product 2 is isolated after chromatography with a gradient from 0 to 4% of MeOH in DCM followed by salification.

LCMS: MH⁺=637
¹H NMR (500 MHz, DMSO-d₆) δ ppm: see Table II

Example 3

N-[(1S,2R)-1-(3,5-difluorobenzyl)-2-hydroxy-3-{[(1S)-7-(trifluoromethyl)-1,2,3,4-tetrahydronaphthalen-1-yl]amino}propyl]-1-ethyl-5-[(2-propylpiperidin-1-yl)carbonyl]-1H-pyrazole-3-carboxamide (compound 64, Table I)

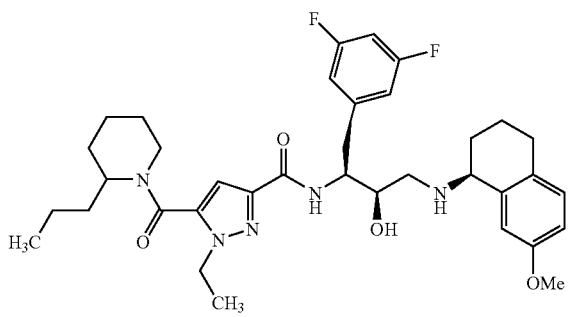 [SMILES: CCCC1CCCCN1C(=O)c1cc(C(=O)N[C@@H](Cc2cc(F)cc(F)c2)[C@H](O)CN[C@H]2CCCc3ccc(OC)cc32)nn1CC]

Following the same procedure as for product 1 and using 0.13 g of the acid of formula (II) 1.4, 0.07 g of HOBt, 0.09 g of EDAC and 0.18 g of the amine of formula (III) 6.2 in 7 ml of DMF, 0.17 g of the hydrochloride of product 3 is isolated after chromatography with a gradient from 0 to 3% of MeOH in DCM followed by salification.

LCMS: MH$^+$=652

$^1$H NMR (500 MHz, DMSO-d$_6$) δ ppm: see Table I.

In Table I that now follows:

Me=methyl,

Ph=phenyl,

TABLE I (Iter)

| | NR₁R₂ | R₃ | X | Y | $R_4, R_5$ ... Q, N—(W)$_n$ | ¹H NMR δ ppm (500 MHz, DMSO-d₆) **If 600 MHz and DMSO-d₆ |
|---|---|---|---|---|---|---|
| 1 | Me—N(CH₂CH₂Me)(CH₂CH₂Me) | Et | H | H | 3-CF₃ phenyl with gem-dimethyl (R₄=R₅=Me) | 0.75 (m, 3H), 0.91 (m, 3H), 1.36 (m, 3H), 1.52 (m, 2H), 2.90 (m, 2H), 3.13 (m, 2H), 3.39 (m, 2H), 3.92 (m, 1H), 4.13 (m, 1H), 4.17 (m, 2H), 4.32 (m, 2H), 5.86 (bs, 1H), 6.68 (s, 1H), 7.14 (m, 1H), 7.23 (m, 4H), 7.64 (t, 1H), 7.76 (d, 1H), 7.82 (d, 1H), 7.95 (s, 1H), 8.14 (d, 1H), 9.09 (bs, 2H) |
| 2 | Me—N(CH₂CH₂Me)(CH₂CH₂Me) | Et | H | H | 3-OMe phenyl with gem-dimethyl (R₄=R₅=Me) | 0.49 (m, 3H), 0.65 (m, 3H), 1.09 (t, 3H), 1.27 (m, 2H), 1.35 (m, 2H), 2.59 (m, 1H), 2.63 (d, 1H), 2.70 (d, 1H), 2.87 (m, 1H), 2.97 (m, 2H), 3.14 (m, 2H), 3.50 (s, 3H), 3.66 (m, 1H), 3.91 (m, 5H), 5.58 (bs, 1H), 6.42 (s, 1H), 6.68 (m, 1H), 6.79 (m, 2H), 6.94 (m, 2H), 6.97 (m, 3H), 7.06 (m, 2H), 7.85 (d, 1H), 8.68 (bs, 2H) |
| 3 | CH₃—N(CH₂CH₂CH₃)(CH₂CH₂CH₃) | Et | prop-2-en-1-yloxy | H | 3-CF₃ phenyl with 1-methylcyclopropyl | 0.81 (m, 3H), 0.98 (m, 1H), 1.28 (m, 1H), 1.41 (m, 4H), 1.64 (m, 6H), 2.80 (m, 1H), 2.90 (t, 1H), 3.07 (m, 1H), 3.29 (m, 2H), 3.45 (m, 2H), 3.97 (m, 1H), 4.10 (m, 1H), 4.23 (m, 2H), 4.51 (m, 2H), 5.27 (d, 1H), 5.37 (d, 1H), 5.89 (d, 1H), 6.04 (m, 1H), 6.70 (s, 1H), 6.76 (d, 1H), 6.78 (s, 1H), 6.82 (s, 1H), 7.17 (t, 1H), 7.63 (m, 1H), 7.78 (m, 1H), 7.80 (m, 1H), 8.01 (s, 1H), 8.13 (d, 1H), 9.47 (bs, 1H), 9.60 (bs, 1H) |

TABLE 1-continued (Iter)

| | NR₁R₂ | R₃ | X | Y | Q | ¹H NMR δ ppm (500 MHz, DMSO-d₆) **1f 600 MHz and DMSO-d₆ |
|---|---|---|---|---|---|---|
| 4 | CH₃-N(CH₂CH₂-)₂ with CH₃ groups | Et | H | benzyl-4-oxy | 3-CF₃ phenyl with 1-methylcyclopropyl | 0.63 (m, 3H), 0.79 (m, 3H), 1.10 (m, 1H), 1.23 (m, 4H), 1.45 (m, 6H), 2.66 (m, 2H), 2.79 (m, 2H), 3.11 (m, 2H), 3.28 (m, 2H), 3.76 (m, 1H), 3.89 (m, 1H), 4.05 (m, 2H), 5.69 (d, 1H), 6.25 (s, 1H), 6.70 (d, 2H), 6.99 (d, 2H), 7.20 (m, 1H), 7.27 (m, 4H), 7.45 (m, 1H), 7.59 (m, 1H), 7.71 (m, 1H), 7.83 (s, 1H), 7.92 (d, 1H), 9.30 (bs, 1H), 9.47 (bs, 1H) |
| 5 | Me-N(CH₂CH₂-)₂ with Me groups | Et | 3-F | 5-F | 3-CF₃ phenyl | ** 0.72 (m, 3H), 0.89 (m, 3H), 1.33 (t, 3H), 1.49 (m, 2H), 1.58 (m, 2H), 2.89 (m, 2H), 3.12 (m, 2H), 3.20 (m, 2H), 3.37 (m, 2H), 3.92 (m, 1H), 4.18 (m, 2H), 4.28 (m, 2H), 5.87 (d, 1H), 6.67 (s, 1H), 6.95 (m, 3H), 7.63 (t, 1H), 7.74 (d, 1H), 7.82 (d, 1H), 7.94 (s, 1H), 8.155 (d, 1H), 8.98 (bs, 1H), 9.16 (bs, 1H) |
| 6 | Me-N(CH₂CH₂-)₂ with Me groups | benzyl | H | H | 3-CF₃ phenyl | 0.59 (m, 3H), 0.82 (m, 3H), 1.25 (m, 2H), 1.48 (m, 2H), 2.87 (m, 2H), 2.99 (m, 2H), 3.11 (m, 2H), 3.27 (m, 2H), 3.95 (m, 2H), 4.08 (m, 1H), 4.27 (m, 2H), 5.40 (s, 2H), 5.90 (d, 1H), 6.73 (s, 1H), 7.17 (m, 7H), 7.33 (m, 3H), 7.62 (t, 1H), 7.74 (d, 1H), 7.81 (d, 1H), 7.95 (s, 1H), 8.16 (d, 1H), 9.03 (bs, 1H), 9.24 (bs, 1H) |

TABLE 1-continued (Iter)

| | NR₁R₂ | R₃ | X | Y | structure | ¹H NMR δ ppm (500 MHz, DMSO-d₆) **If 600 MHz and DMSO-d₆ |
|---|---|---|---|---|---|---|
| 7 | Me-N(CH₂CH₂CH₂Me)₂ (dimethyl bis-propyl amine) | Et | H | H | 3-CF₃, 5-Et phenyl | ** 0.77 (m, 3H), 0.91 (m, 3H), 1.13 (m, 2H), 1.31 (m, 5H), 1.45 (m, 2H), 1.54 (m, 2H), 2.87 (m, 2H), 3.08 (m, 2H), 3.24 (m, 2H), 3.39 (m, 2H), 3.87 (m, 1H), 4.12 (m, 3H), 4.27 (m, 2H), 5.85 (bs, 1H), 6.65 (s, 1H), 7.11 (m, 1H), 7.20 (m, 4H), 7.61 (t, 1H), 7.73 (d, 1H), 7.80 (d, 1H), 7.93 (s, 1H), 8.06 (d, 1H), 8.98 (bs, 1H), 9.16 (bs, 1H) |
| 8 | CH₃CH₂CH(NH—)CH₂CH₂Me | Et | H | H | 3-CF₃, 5-Et phenyl | 0.83 (m, 6H), 1.27 (m, 7H), 1.40 (m, 4H), 2.85 (m, 2H), 3 (d, 1H), 3.17 (d, 1H), 3.88 (m, 2H), 4.09 (m, 1H), 4.22 (m, 2H), 4.48 (m, 2H), 5.83 (bs, 1H), 7.11 (m, 2H), 7.20 (m, 4H), 7.60 (t, 1H), 7.70 (d, 1H), 7.77 (d, 1H), 7.89 (s, 1H), 8.08 (d, 1H), 8.13 (d, 1H), 9.00 (bs, 2H) |
| 9 | cyclopropyl-NH— | Et | H | H | 3-CF₃, 5-Et phenyl | ** 0.54 (m, 2H), 0.68 (m, 2H), 1.33 (t, 3H), 2.84 (m, 3H), 3.07 (m, 2H), 3.93 (m, 1H), 4.11 (m, 1H), 4.25 (m, 2H), 4.52 (m, 2H), 5.85 (bs, 1H), 7.11 (m, 2H), 7.19 (m, 4H), 7.62 (t, 1H), 7.73 (d, 1H), 7.80 (d, 1H), 7.93 (s, 1H), 8.05 (d, 1H), 8.50 (s, 1H), 8.99 (bs, 1H), 9.19 (bs, 1H) |

TABLE 1-continued (Iter)

| | NR₁R₂ | R₃ | X | Y | R₄, R₅, Q, C,N-(W)ₙ | ¹H NMR δ ppm (500 MHz, DMSO-d₆) **If 600 MHz and DMSO-d₆ |
|---|---|---|---|---|---|---|
| 10 | cyclopropyl-N-CH₂CH₂CH₂-Me | Et | H | H | 3-CF₃, ethyl-phenyl | 0.48 (m, 2H), 0.63 (m, 2H), 0.91 (m, 3H), 1.33 (m, 5H), 1.58 (m, 2H), 2.88 (m, 3H), 3.11 (m, 2H), 3.43 (m, 2H), 3.94 (m, 1H), 4.09 (m, 1H), 4.25 (m, 4H), 5.89 (d, 1H), 6.90 (m, 1H), 7.12 (m, 1H), 7.21 (m, 4H), 7.62 (t, 1H), 7.74 (d, 1H), 7.81 (d, 1H), 7.94 (s, 1H), 8.06 (d, 1H), 8.99 (bs, 1H), 9.18 (bs, 1H) |
| 11 | H-N-CH₂CH₂CH₂-Me | Et | H | H | 3-CF₃, ethyl-phenyl | **0.87 (t, 3H), 1.30 (m, 5H), 1.46 (m, 2H), 2.87 (m, 2H), 3.08 (m, 2H), 3.22 (m, 2H), 3.92 (m, 1H), 4.11 (m, 1H), 4.24 (m, 2H), 4.51 (m, 2H), 5.85 (bs, 1H), 7.10 (m, 2H), 7.18 (m, 4H), 7.62 (t, 1H), 7.73 (d, 1H), 7.79 (m, 1H), 7.92 (s, 1H), 8.06 (d, 1H), 8.49 (m, 1H), 8.99 (bs, 1H), 9.13 (bs, 1H) |
| 12 | H-N-CH₂CH₂CH₂CH₂CH₂-Me | Et | H | H | 3-CF₃, ethyl-phenyl | **0.85 (m, 9H), 1.29 (m, 9H), 1.47 (m, 2H), 2.87 (m, 2H), 3.08 (m, 2H), 3.18 (m, 2H), 3.93 (m, 1H), 4.10 (m, 1H), 4.24 (m, 2H), 4.51 (m, 2H), 5.84 (d, 1H), 7.11 (m, 2H), 7.19 (m, 4H), 7.66 (t, 1H), 7.73 (d, 1H), 7.80 (d, 1H), 7.92 (s, 1H), 8.07 (d, 1H), 8.50 (m, 1H), 8.99 (bs, 1H), 9.17 (bs, 1H) |

TABLE 1-continued (Iter)

| | NR₁R₂ | R₃ | X | Y | R₄, R₅, Q, C,N—(W)ₙ phenyl | ¹H NMR δ ppm (500 MHz, DMSO-d₆) **If 600 MHz and DMSO-d₆ |
|---|---|---|---|---|---|---|
| 13 | Me-N(Me)-CH₂CH₂CH₂CH₂-Me | Et | H | H | 3-CF₃, 5-Et phenyl | **0.79 (m, 1H), 0.87 (m, 2H), 1.07 (m, 1H), 1.18 (m, 1H), 1.26 (m, 1H), 1.32 (m, 4H), 1.49 (m, 1H), 1.55 (m, 1H), 2.86 (m, 2H), 3.08 (m, 2H), 3.28 (m, 1H), 3.28 (m, 1H), 3.42 (m, 1H), 3.92 (m, 1H), 4.09 (m, 1H), 4.17 (m, 2H) 4.25 (m, 2H), 5.85 (bs, 1H), 6.73 (s, 1H), 7.12 (m, 1H), 7.20 (m, 4H), 7.61 (t, 1H), 7.73 (d, 1H), 7.80 (d, 1H), 7.92 (s, 1H), 8.07 (d, 1H), 8.99 (bs, 1H), 9.18 (bs, 1H) |
| 14 | cyclopropyl-N(Me)-CH₂CH₂CH₂CH₂-Me | Et | H | H | 3-CF₃, 5-Et phenyl | **0.48 (m, 2H), 0.62 (m, 2H), 0.85 (s, 3H), 1.27 (m, 7H), 1.58 (m, 2H), 2.87 (m, 3H), 3.09 (m, 2H), 3.41 (m, 2H), 3.93 (m, 1H), 4.09 (m, 1H), 4.21 (m, 2H), 4.28 (m, 2H), 5.87 (bs, 1H), 6.87 (m, 1H), 7.11 (m, 1H), 7.22 (m, 4H), 7.62 (t, 1H), 7.73 (d, 1H), 7.80 (d, 1H), 7.93 (s, 1H), 8.03 (d, 1H), 8.97 (bs, 1H), 9.15 (bs, 1H) |
| 15 | Me-N(Me)-CH₂CH₂CH₂CH₂CH₂CH₂-Me | Et | H | H | 3-CF₃, 5-Et phenyl | **0.84 (m, 3H), 1.22 (m, 11H), 1.53 (m, 2H), 2.87 (m, 2H), 2.96 (s, 3H), 3.08 (m, 2H), 3.30 (m, 2H), 3.43 (m, 1H), 3.92 (m, 1H), 4.20 (m, 4H), 5.83 (bs, 1H), 6.74 (s, 1H), 7.12 (m, 1H), 7.21 (m, 4H), 7.61 (t, 1H), 7.73 (d, 1H), 7.80 (d, 1H), 7.9 (s, 1H), 8.08 (d, 1H), 9.04 (bs, 2H) |

TABLE 1-continued (Iter)

[Structure shown: core compound with R1, R2, R3, R4, R5, Q, W, X, Y substituents on pyrazole-diamide scaffold with hydroxyl and benzyl groups]

| | NR₁R₂ | R₃ | X | Y | [Ar group] | ¹H NMR δ ppm (500 MHz, DMSO-d₆) **If 600 MHz and DMSO-d₆ |
|---|---|---|---|---|---|---|
| 16 | N-Me, (CH₂)₄-Me | Et | H | H | 3-CF₃-phenyl-ethyl | **0.84 (m, 3H), 1.23 (m, 9H), 1.53 (m, 2H), 2.92 (m, 2H), 3.08 (s, 3H), 3.12 (m, 2H), 3.31 (m, 1H), 3.44 (m, 1H), 3.94 (m, 1H), 4.11 (m, 1H), 4.18 (m, 2H), 4.27 (m, 2H), 5.88 (bs, 1H), 6.75 (s, 1H), 7.13 (m, 1H), 7.23 (m, 4H), 7.63 (dd, 1H), 7.75 (d, 1H), 7.82 (d, 1H), 7.95 (s, 1H), 8.09 (d, 1H), 8.99 (bs, 1H), 9.19 (bs, 1H) |
| 17 | N-CH₃, (CH₂)₄-CH₃ | Et | 3-F | 5-F | 7-OMe-tetralin-1-yl (Me) | 0.83 (m, 3H), 1.15 (m, 3H), 1.33 (m, 6H), 1.49 (m, 1H), 1.56 (m, 1H), 1.68 (m, 1H), 1.92 (m, 1H), 2.03 (m, 2H), 2.66 (m, 2H), 2.84 (m, 1H), 2.96 (m, 4H), 3.14 (m, 2H), 3.30 (m, 1H), 3.44 (m, 1H), 3.73 (s, 3H), 3.97 (m, 1H), 4.19 (m, 3H), 4.52 (m, 1H), 5.91 (bs, 1H), 6.79 (s, 1H), 6.87 (m, 1H), 6.97 (m, 3H), 7.11 (m, 2H), 8.24 (d, 1H), 8.79 (bs, 1H), 8.90 (bs, 1H) |

TABLE 1-continued

| | NR₁R₂ | R₃ | X | Y | R₄,R₅,Q,(W)ₙ | ¹H NMR δ ppm (500 MHz, DMSO-d₆) **If 600 MHz and DMSO-d₆ |
|---|---|---|---|---|---|---|
| 18 | N(CH₃)(CH₂CH₂OCH₃) | Et | 3-F | 5-F | (S)-7-methoxy-1-methyl-tetralin | 1.11 (t, 3H), 1.33 (m, 3H), 1.70 (m, 2H), 1.80 (m, 1H), 1.91 (m, 1H), 2.01 (m, 2H), 2.66 (m, 2H), 2.83 (m, 1H), 2.96 (m, 4H), 3.14 (d, 2H), 3.25 (m, 2H), 3.41 (m, 3H), 3.49 (m, 1H), 3.72 (s, 3H), 3.94 (m, 1H), 4.17 (m, 3H), 4.50 (m, 1H), 5.87 (d, 1H), 6.79 (s, 1H), 6.88 (d, 1H), 6.97 (m, 3H), 7.10 (m, 2H), 8.23 (d, 1H), 8.76 (bs, 1H), 8.85 (bs, 1H) |
| 19 | N(CH₃)(CH₂CH₂CH₂CH₂CH₂-cyclopropyl) | Et | 3-F | 5-F | 1-(1-methylcyclopropyl)-3-CF₃-phenyl | 0.48 (m, 2H), 0.6 (m, 2H), 0.87 (m, 4H), 1.29 (m, 10H), 1.57 (m, 4H), 2.72 (m, 1H), 2.90 (m, 2H), 3.06 (m, 1H), 3.44 (m, 3H), 3.90, (m, 1H), 4.05 (m, 1H), 4.23 (m, 2H), 5.86 (d, 1H), 6.95 (m, 4H), 7.57 (dd, 1H), 7.84 (d, 1H), 7.96 (s, 1H), 8.14 (d, 1H), 9.38 (bs, 1H), 9.60 (bs, 1H) |
| 20 | N(CH₃)(CH₂CH₂CH₂CH₂CH₂CH₂Me) | Et | 3-F | 5-F | 1-(1-methylcyclopropyl)-3-CF₃-phenyl | 0.85 (m, 3H), 1.09 (m, 1H), 1.19 (m, 4H), 1.32 (m, 8H), 1.46 (m, 4H), 2.72 (m, 1H), 2.89 (m, 1H), 2.97 (m, 4H), 3.06 (m, 1H), 3.30 (m, 1H), 3.45 (m, 1H), 3.89 (m, 1H), 4.05 (m, 1H), 4.18 (m, 2H), 5.86 (bs, 1H), 6.73 (s, 1H), 6.94 (m, 3H), 7.56 (m, 1H), 7.70 (d, 1H), 7.83 (d, 1H), 7.95 (s, 1H) 8.16 (d, 1H), 9.36 (bs, 1H) 9.59 (bs, 1H) |

TABLE 1-continued (Iter)

| | NR₁R₂ | R₃ | X | Y | | ¹H NMR δ ppm (500 MHz, DMSO-d₆) **If 600 MHz and DMSO-d₆ |
|---|---|---|---|---|---|---|
| 21 | CH₃-N-(CH₂)₅-Me | Et | 3-F | 5-F | tetrahydronaphthalene with OMe and Me | 0.73-0.80 (2 t, 3H), 1.00 (m, 1H), 1.10 (m, 3H), 1.24 (m, 8H), 1.42 (m, 1H), 1.48 (m, 1H), 1.62 (m, 1H), 1.84 (m, 1H), 1.96 (m, 1H), 2.59 (m, 2H), 2.77 (m, 1H), 2.88 (m, 4H), 3.07 (m, 2H), 3.23 (m, 1H), 3.37 (t, 1H), 3.65 (s, 3H), 3.88 (m, 1H) 4.11 (m, 3H), 4.44 (m, 1H), 5.83 (bs, 1H), 6.72 (s, 1H), 6.80 (d, 1H), 6.90 (m, 3H), 7.02 (d, 1H), 7.06 (s, 1H), 8.17 (d, 1H), 8.68 (bs, 1H), 8.80 (bs, 1H) |
| 22 | cyclopropyl-N(Me)-(CH₂)₃-OH | Et | H | H | 3-CF₃ phenyl with ethyl | 0.56 (m, 2H), 0.68 (m, 2H), 1.39 (t, 3H), 1.82 (m, 2H), 2.95 (m, 2H), 3.16 (t, 2H), 3.49 (m, 4H), 3.99 (m, 1H), 4.16 (m, 1H), 4.31 (m, 4H), 4.59 (bs, 1H), 5.97 (bs 1H), 6.98 (m, 1H), 7.19 (m, 1H), 7.27 (m, 4H), 7.70 (dd, 1H), 7.82 (d, 1H), 7.88 (d, 1H), 8.02 (s, 1H), 8.16 (d, 1H),9.08 (bs, 1H), 9.24 (bs, 1H) |
| 23 | cyclopropyl-N(Me)-(CH₂)₄-OH | Et | H | H | 3-CF₃ phenyl with ethyl | **0.50 (m, 2H), 0.64 (m, 2H), 1.34 (t, 3H), 1.44 (m, 2H), 1.65 (m, 2H), 2.89 (m, 3H), 3.11 (m, 2H), 3.43 (m, 4H), 3.94 (m, 1H), 4.12 (m, 1H), 4.23 (m, 2H), 4.28 (m, 2H), 4.41 (t, 1H), 5.87 (bs, 1H), 6.89 (m, 1H), 7.13 (dd, 1H), 7.22 (m, 4H), 7.63 (t, 1H), 7.75 (d,1H), 7.81 (d,1H), 7.95 (s, 1H), 8.05 (d, 1H), 8.95 (bs, 1H), 9.13 (bs, 1H) |

TABLE 1-continued (Iter)

| # | NR$_1$R$_2$ | R$_3$ | X | Y | Ar | $^1$H NMR δ ppm (500 MHz, DMSO-d$_6$) **If 600 MHz and DMSO-d$_6$ |
|---|---|---|---|---|---|---|
| 24 | cyclopropyl-N(Me)-(CH$_2$)$_5$-OH | Et | H | H | 3-CF$_3$-phenyl | 0.49 (m, 2H), 0.62 (m, 2H), 1.33 (m, 5H), 1.46 (m, 2H), 1.61 (m, 2H), 2.88 (m, 3H), 3.10 (m, 2H), 3.41 (m, 4H), 3.93 (m, 1H), 4.11 (m, 1H), 4.25 (m, 4H), 4.40 (t, 1H), 5.90 (bs, 1H), 6.93 (m, 1H), 7.13 (t, 1H), 7.21 (m, 4H), 7.63 (dd, 1H), 7.76 (d, 1H), 7.81 (d, 1H), 7.95 (s, 1H), 8.11 (d, 1H), 8.98 (bs, 1H), 9.15 (bs, 1H) |
| 25 | cyclopropyl-N(Me)-(CH$_2$)$_3$-OEt | Et | H | H | 3-CF$_3$-phenyl | **0.49 (m, 2H), 0.62 (m, 2H), 1.08 (m, 3H), 1.32 (t, 3H), 1.82 (m, 2H), 2.89 (m, 3H), 3.11 (m, 2H), 3.39 (m, 4H), 3.48 (m, 2H), 3.93 (m, 1H), 4.09 (m, 1H), 4.22 (q, 2H), 4.29 (m, 2H), 5.87 (bs 1H), 6.89 (m, 1H), 7.12 (t, 1H), 7.20 (m, 4H), 7.62 (dd, 1H), 7.74 (d, 1H), 7.80 (d, 1H), 7.94 (s, 1H), 8.03 (d, 1H), 8.97 (bs, 1H), 9.15 (bs, 1H) |
| 26 | cyclopropyl-N(Me)-(CH$_2$)$_3$-OEt | Et | 3-F | 5-F | 6-OMe-tetrahydronaphthyl | 0.47 (m, 2H), 0.60 (m, 2H), 1.09 (m, 3H), 1.33 (t, 3H), 1.67 (m, 1H), 1.87 (m, 3H), 2.02 (m, 2H), 2.67 (m, 2H), 2.89 (m, 3H), 3.13 (d, 2H), 3.40 (m, 6H), 3.95 (m, 1H), 4.13 (m, 1H), 4.22 (m, 2H), 4.51 (m, 1H), 5.91 (d, 1H), 6.86 (d, 1H), 6.97 (m, 4H), 7.09 (d, 1H), 7.13 (s, 1H), 8.21 (d, 1H), 8.79 (bs, 1H), 8.90 (bs, 1H) |

TABLE 1-continued

| | NR₁R₂ | R₃ | X | Y | | ¹H NMR δ ppm (500 MHz, DMSO-d₆) **If 600 MHz and DMSO-d₆ |
|---|---|---|---|---|---|---|
| 27 | 2-ethylphenyl-NH-Me | Et | H | H | 3-ethylphenyl, CF₃ | 1.11 (t, 3H), 1.35 (t, 3H), 2.60 (m, 2H), 2.90 (m, 2H), 3.11 (m, 2H), 3.95 (m, 1H), 4.13 (m, 1H), 4.28 (m, 2H), 4.54 (q, 2H), 5.90 (bs, 1H), 7.13 (m, 1H), 7.24 (m, 7H), 7.29 (m, 1H), 7.30 (m, 1H), 7.64 (dd, 1H), 7.74 (d, 1H), 7.81 (d, 1H), 7.94 (s, 1H), 8.18 (d, 1H), 8.99 (bs, 1H), 9.18 (bs, 1H), 9.98 (s. 1H) |
| 28 | N-methyl-N-(3-(2-ethylphenyl)propyl) | Et | H | H | 3-ethylphenyl, CF₃ | 0.88 (t, 3H), 1.03 (m, 3H), 1.31 (m, 2H), 1.40 (m, 3H), 1.52 (m, 2H), 2.36 (m, 1H), 2.51 (m, 1H), 2.79 (m, 2H), 3.01 (m, 2H), 3.36 (m, 1H), 3.86 (m, 1H), 3.96 (m, 2H), 4.22 (m, 2H), 4.39 (m, 2H), 5.81 (bs, 1H), 7.10–7.25 (m, 8H), 7.33 (m, 2H), 7.60 (m, 1H), 7.76 (m, 2H), 7.92 (m, 2H), 8.92 (bs, 1H), 9.08 (bs. 1H) |
| 29 | 4-methylmorpholine | Et | H | H | 3-ethylphenyl, CF₃ | 1.35 (t, 3H), 2.89 (m, 2H), 3.10 (m, 2H), 3.46–3.63 (m, 8H), 3.92 (m, 1H), 4.11 (m, 1H), 4.29 (m, 4H), 5.87 (bs, 1H), 6.73 (s, 1H), 7.13 (m, 1H), 7.21 (m, 4H), 7.62 (m, 1H), 7.74 (d, 1H), 7.81 (d, 1H), 7.94 (s, 1H), 8.12 (d, 1H), 9.08 (bs, 2H) |

TABLE 1-continued (Iter)

| | NR₁R₂ | R₃ | X | Y | [aryl group] | ¹H NMR δ ppm (500 MHz, DMSO-d₆) **If 600 MHz and DMSO-d₆ |
|---|---|---|---|---|---|---|
| 30 | [1-methyl-2-methyl-5-ethyl piperidine] | Et | H | H | 3-CF₃, 5-ethyl phenyl | **0.82 (m, 3H), 1.15-1.87 (m, 16H), 2.86 (m, 2H), 3.09 (m, 2H), 3.92 (d, 1H), 4.12 (m, 3H), 4.27 (m, 2H), 5.88 (s, 1H), 6.62 (s, 1H), 7.17 (m, 5H), 7.61 (m, 1H), 7.72 (d, 1H), 7.80 (d, 1H), 7.93 (s, 1H), 8.07 (m, 1H), 8.99 (bs, 1H), 9.20 (bs, 1H) |
| 31 | [1-methyl-2-propyl piperidine] | —(CH₂)₃—CH₃ | H | H | 3-CF₃, 5-ethyl phenyl | 0.81-1.77 (m, 20H), 2.89 (m, 2H), 3.10 (m, 3H), 3.50 (m, 1H), 3.94 (m, 1H), 4.13 (m, 3H), 4.27 (m, 2H), 4.50-4.73 (m, 1H), 5.88 (bs, 1H), 6.64 (s, 1H), 7.14 (m, 1H), 7.24 (m, 4H), 7.64 (m, 1H), 7.75 (d, 1H), 7.82 (d, 1H), 7.95 (s, 1H), 8.12 (m, 1H), 9.08 (bs, 2H) |
| 32 | [1-methyl-2-propyl piperidine] | [benzyl/phenethyl] | H | H | 3-CF₃, 5-ethyl phenyl | 0.72-1.70 (m, 13H), 2.74-2.98 (m, 3H), 3.14 (m, 2H), 3.34 (m, 1H), 3.92 (m, 1H), 4.12 (m, 1H), 4.30 (m, 2H), 4.64 (m, 1H), 5.46 (s, 2H), 5.90 (bs, 1H), 6.72 (s, 1H), 7.19 (m, 7H), 7.36 (m, 3H), 7.65 (m, 1H), 7.77 (d, 1H), 7.83 (d, 1H), 7.97 (s, 1H), 8.21 (d, 1H), 8.96 (bs, 1H), 9.14 (bs, 1H) |

TABLE 1-continued (Iter)

| | NR₁R₂ | R₃ | [structure with R₄,R₅,Q,C,N,(W)n, CF₃] | X | Y | ¹H NMR δ ppm (500 MHz, DMSO-d₆) **If 600 MHz and DMSO-d₆ |
|---|---|---|---|---|---|---|
| 33 | N-methylpiperidine with CH₃ propyl | Et | 3-ethylphenyl with CF₃ | H | H | 0.77-1.80 (m, 16H), 2.84 (m, 2H), 3.10 (m, 3H), 3.50 (m, 1H), 3.92 (m, 1H), 4.12 (m, 3H), 4.28 (m, 2H), 4.71 (m, 1H), 5.90 (d, 1H), 6.62 (s, 1H), 7.22 (m, 5H), 7.62 (m, 1H), 7.74 (d, 1H), 7.81 (d, 1H), 7.94 (s, 1H), 8.11 (d, 1H), 8.99 (bs, 1H), 9.19 (bs, 1H) |
| 34* Isomer A | N-methylpiperidine with CH₃ propyl | Et | 3-ethylphenyl with CF₃ | H | H | 0.70-1.85 (m, 16H), 2.87 (m, 2H), 3.11 (m, 3H), 3.48 (m, 1H), 3.94 (m, 1H), 4.15 (m, 3H), 4.27 (m, 2H), 4.72 (m, 1H), 5.90 (d, 1H), 6.64 (s, 1H), 7.14 (m, 1H), 7.22 (m, 4H), 7.63 (m, 1H), 7.74 (d, 1H), 7.83 (d, 1H), 7.96 (s, 1H), 8.12 (d, 1H), 9.09 (bs, 2H) |
| 35* Isomer B | N-methylpiperidine with CH₃ propyl | Et | 3-ethylphenyl with CF₃ | H | H | 0.70-1.85 (m, 16H), 2.90 (m, 2H), 3.13 (m, 3H), 3.50 (m, 1H), 3.96 (m, 1H), 4.14 (m, 3H), 4.28 (m, 2H), 4.72 (m, 1H), 5.94 (bs, 1H), 6.63 (s, 1H), 7.14 (m, 1H), 7.23 (m, 4H), 7.63 (m, 1H), 7.75 (d, 1H), 7.84 (d, 1H), 7.97 (s, 1H), 8.11 (d, 1H), 9.04 (bs, 1H), 9.30 (bs, 1H) |
| 36 | N-methylpiperidine with CH₃ propyl | Et | phenyl | H | H | 0.7-1.87 (m, 16H), 2.89 (m, 2H), 3.05 (d, 1H), 3.15 (m, 2H), 3.52 (m, 1H), 3.95 (m, 1H), 4.17 (m, 5H), 4.75 (m, 1H), 5.88 (bs, 1H), 6.68 (s, 1H), 7.18 (m, 1H), 7.25 (m, 4H), 7.40 (m, 3H), 7.53 (m, 2H), 8.13 (m, 1H), 9.00 (bs, 2H) |

TABLE 1-continued (Iter)

| | NR$_1$R$_2$ | R$_3$ | X | Y | | $^1$H NMR δ ppm (500 MHz, DMSO-d$_6$) **If 600 MHz and DMSO-d$_6$ |
|---|---|---|---|---|---|---|
| 37 | N-methylpiperidine-2-propyl | Et | H | H | 3-CF$_3$, 4-F phenethyl | 0.7-1.85 (m, 16H), 2.88 (m, 2H), 3.11 (m, 3H), 3.51 (m, 1H), 3.92 (m, 1H), 4.19 (m, 5H), 4.74 (m, 1H), 5.90 (bs, 1H), 6.65 (s, 1H), 7.16 (m, 1H), 7.23 (m, 4H), 7.58 (m, 1H), 7.90 (m, 1H), 8.03 (d, 1H), 8.13 (m, 1H), 8.96 (bs, 1H), 9.16 (s, 1H) |
| 38 | N-methylpiperidine-2-propyl | Et | H | H | 4-F phenethyl | 0.79-1.88 (m, 16H), 2.86 (m, 2H), 3.03 (m, 1H), 3.08 (m, 1H), 3.14 (m, 1H), 3.52 (m, 1H), 3.93 (m, 1H), 4.16 (m, 5H), 4.73 (m, 1H), 5.87 (bs, 1H), 6.66 (s, 1H), 7.15 (m, 1H), 7.27 (m, 6H), 7.57 (m, 2H), 8.12 (d, 1H), 8.94 (bs, 2H) |
| 39 | N-methylpiperidine-2-propyl | Et | H | H | 3,5-diF phenethyl | 0.77-1.90 (m, 16H), 2.85 (m, 2H), 3.02 (m, 1H), 3.11 (m, 2H), 3.48 (m, 1H), 3.91 (m, 1H), 4.09 (m, 1H), 4.17 (m, 4H), 4.71 (m, 1H), 5.88 (bs, 1H), 6.61 s, 1H), 7.12 (m, 1H), 7.24 (m, 7H), 8.10 (d, 1H), 8.98 (bs, 1H), 9.26 (bs, 1H) |
| 40 | N-methylpiperidine-2-propyl | Et | H | H | 3-Br phenethyl | 0.77-1.77 (m, 16H), 2.85 (m, 2H), 3.04 (m, 1H), 3.10 (m, 2H), 3.48 (m, 1H), 3.92 (m, 1H), 4.09 (m, 1H), 4.17 (m, 4H), 4.71 (m, 1H), 5.88 (bs, 1H), 6.63 (s, 1H), 7.12 (m, 1H), 7.20 (m, 4H), 7.33 (m, 1H), 7.51 (d, 1H), 7.77 (s, 1H), 8.10 (d, 1H), 8.95 (bs, 1H), 9.18 (bs, 1H) |

TABLE 1-continued (Iter)

| | NR₁R₂ | R₃ | X | Y | (structure) | ¹H NMR δ ppm (500 MHz, DMSO-d₆) **If 600 MHz and DMSO-d₆ |
|---|---|---|---|---|---|---|
| 41 | 1-methyl-2-(propyl)piperidine | Et | H | H | Me (phenyl) | 0.86-1.62 (m, 16H), 2.27 (s, 3H), 2.89 (m, 2H), 3.01 (m, 1H), 3.11 (m, 2H), 3.49 (m, 1H), 3.92 (m, 1H), 4.13 (m, 5H), 4.71 (m, 1H), 5.87 (bs, 1H), 6.63 (s, 1H), 7.21 (m, 9H), 8.10 (bs, 1H), 8.87 (bs, 1H), 9.03 (bs, 1H) |
| 42 | 1-methyl-2-(propyl)piperidine | Et | H | H | Me, F (phenyl) | 0.86-1.58 (m, 16H), 2.19 (s, 3H), 2.85 (m, 2H), 2.99 (m, 1H), 3.11 (m, 2H), 3.47 (m, 1H), 3.89 (m, 1H), 4.13 (m, 5H), 4.71 (m, 1H), 5.86 (bs, 1H), 6.63 (s, 1H), 7.12 (m, 2H), 7.25 (m, 4H), 7.35 (m, 1H), 7.41 (m, 1H), 8.09 (d, 1H), 8.97 (bs, 2H) |
| 43 | 1-methyl-2-(propyl)piperidine | Et | H | H | COOH (phenyl) | 0.77-1.77 (m, 16H), 2.76 (m, 1H), 2.86 (m, 1H), 2.92 (m, 1H), 3.03 (m, 2H), 3.47 (m, 1H), 3.84 (m, 1H), 4.14 (m, 5H), 4.70 (m, 1H), 5.69 (bs, 1H), 6.63 (s, 1H), 7.12 (m, 1H), 7.19 (m, 4H), 7.58 (m, 2H), 7.91 (m, 2H), 8.09 (bs, 1H), 9.20 (bs, 1H) |
| 44 | 1-methyl-2-(propyl)piperidine | Et | H | H | CF₃, CF₃ (phenyl) | 0.78-1.77 (m, 16H), 2.83 (m, 2H), 3.13 (m, 3H), 3.49 (m, 1H), 3.89 (m, 1H), 4.11 (m, 3H), 4.45 (m, 2H), 4.71 (m, 1H), 5.93 (bs, 1H), 6.61 (m, 1H), 7.12 (m, 1H), 7.21 (m, 4H), 8.13 (m, 2H), 8.30 (s, 2H), 9.11 (bs, 1H), 9.40 (bs, 1H) |

TABLE 1-continued (Iter)

| | NR₁R₂ | R₃ | X | Y | R₄, R₅ ... C,N-(W)ₙ | ¹H NMR δ ppm (500 MHz, DMSO-d₆) **If 600 MHz and DMSO-d₆ |
|---|---|---|---|---|---|---|
| 45 | N-methyl-2-(2-propyl)piperidine | Et | H | H | 3-ethylphenyl, OMe | 0.75-1.85 (m, 16H), 2.2.85 (m, 3H), 3.03 (m, 1H), 3.12 (m, 1H), 3.49 (m, 1H), 3.75 (s, 3H), 3.95 (m, 1H), 4.13 (m, 5H), 4.72 (m, 1H), 5.92 (d, 1H), 6.63 (m, 1H), 6.92 (d, 1H), 7.06 (d, 1H), 7.20 (m, 6H), 7.56 (t, 1H), 8.11 (bs, 1H), 8.96 (bs, 1H), 9.24 (bs, 1H) |
| 46 (HCl)₂ | N-methyl-2-(2-propyl)piperidine | Et | H | H | 3-ethylpyridyl | 0.7-1.85 (m, 16H), 2.91 (m, 2H), 3.13 (m, 3H), 3.70 (m, 2H), 3.97 (m, 1H), 4.15 (m, 4H), 4.32 (m, 2H), 4.74 (m, 1H), 6.66 (s, 1H), 7.14 (m, 1H), 7.22 (m, 4H), 7.71 (m, 1H), 8.14 (m, 1H), 8.29 (m, 1H), 8.73 (d, 1H), 8.87 (s, 1H), 9.14 (bs, 1H), 9.50 (bs, 1H) |
| 47 | N-methyl-2-(2-propyl)piperidine | Et | 3-F | 5-F | 3-ethylphenyl, CF₃ | 0.76-1.85 (m, 16H), 2.88 (m, 2H), 3.11 (m, 3H), 3.49 (m, 1H), 3.91 (m, 1H), 4.14 (m, 3H), 4.30 (m, 2H), 4.72 (m, 1H), 5.91 (bs, 1H), 6.65 (s, 1H), 6.98 (m, 3H), 7.64 (m, 1H), 7.76 (d, 1H), 7.82 (d, 1H), 7.95 (s, 1H), 8.23 (d, 1H), 9.01 (bs, 1H), 9.21 (bs, 1H) |
| 48 | N-methyl-2-(2-propyl)piperidine | Et | H | H | (2-phenylpropan-2-yl)phenyl | 0.7-1.85 (m, 22H), 2.5 (m, 1H), 2.65 (m, 1H), 2.82 (m, 1H), 3.00 (m, 1H), 3.15 (m, 1H), 3.47 (m, 1H), 3.82 (m, 1H), 4.02 (m, 1H), 4.16 (m, 2H), 4.71 (m, 1H), 5.80 (d, 1H), 6.59 (s, 1H), 7.15 (m, 5H), 7.32 (m, 3H), 7.56 (d, 2H), 8.04 (m, 1H), 8.94 (bs, 1H), 9.24 (bs, 1H) |

TABLE 1-continued (1ter)

[Structure shown: Core structure with R1-N(R2)-C(=O) connected to pyrazole (N-R3) with second C(=O)-NH linkage to chain containing X-substituted phenyl, OH, and R4/R5-bearing carbon attached to Q, W(n)-substituted aryl C,N ring]

| # | NR₁R₂ | R₃ | X | Y | R₄R₅-C(Q)(C,N-(W)ₙ aryl) | ¹H NMR δ ppm (500 MHz, DMSO-d₆) **If 600 MHz and DMSO-d₆ |
|---|---|---|---|---|---|---|
| 49 | N-methylpiperidin-2-yl-ethyl (N-CH₃ piperidine with ethyl) | Et | H | H | C(Me)(Me)-phenyl-3-CF₃ | 0.7-1.85 (m, 22H), 2.5 (m, 1H), 2.66 (m, 1H), 2.82 (m, 1H), 3.00 (m, 1H), 3.15 (m, 1H), 3.46 (m, 1H), 3.86 (m, 1H), 4.04 (m, 1H), 4.15 (m, 2H), 4.71 (m, 1H), 5.81 (d, 1H), 6.57 (s, 1H), 7.06 (m, 1H), 7.19 (m, 4H), 7.61 (m, 1H), 7.70 (m, 1H), 7.92 (m, 2H), 8.02 (d, 1H), 9.14 (bs, 1H), 9.55 (bs, 1H) |
| 50 | N-methylpiperidin-2-yl-ethyl | Et | 3-F | 5-F | C(Me)(Me)-phenyl-3-CF₃ | 0.7-1.85 (m, 22H), 2.5 (m, 1H), 2.70 (m, 1H), 2.86 (m, 1H), 3.03 (d, 1H), 3.15 (m, 1H), 3.49 (m, 1H), 3.85 (m, 1H), 4.05 (m, 1H), 4.16 (m, 2H), 4.72 (m, 1H), 5.82 (d, 1H), 6.58 (s, 1H), 6.91 (d, 1H), 6.97 (m, 2H), 7.64 (m, 1H), 7.70 (d, 1H), 7.91 (d, 1H), 7.95 (s, 1H), 8.12 (d, 1H), 9.11 (bs, 1H), 9.47 (bs, 1H) |
| 51 | N-methylpiperidin-2-yl with ethyl chain (CH₃ on N, ethyl substituent) | Et | H | H | 1-methylcyclopropyl-phenyl-3-CF₃ | 0.70-1.85 (m, 20H), 2.72 (m, 1H), 2.80 (m, 1H), 2.91 (m, 1H), 3.05 (d, 1H), 3.15 (m, 1H), 3.49 (m, 1H), 3.91 (m, 1H), 4.02 (m, 1H), 4.15 (m, 2H), 4.71 (m, 1H), 5.83 (bs, 1H), 6.57 (s, 1H), 7.11 (m, 1H), 7.20 (m, 4H), 7.54 (m, 1H), 7.67 (m, 1H), 7.82 (m, 1H), 7.93 (s, 1H), 8.05 (d, 1H), 9.40 (bs, 1H), 9.70 (bs, 1H) |

| | NR₁R₂ | R₃ | X | Y | R₄,R₅ | ¹H NMR δ ppm (500 MHz, DMSO-d₆) **If 600 MHz and DMSO-d₆ |
|---|---|---|---|---|---|---|
| 52 | 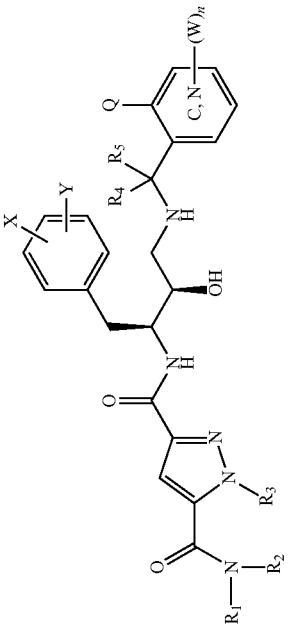 | Et | prop-2-en-1-yloxy | H | 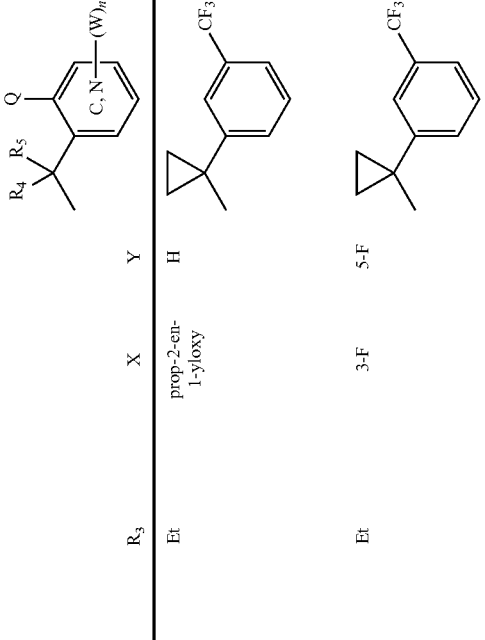 | 0.70-1.85 (m, 20H), 2.58 (m, 1H), 2.66 (m, 1H), 2.77 (m, 1H), 2.85 (m, 1H), 3.00 (m, 1H), 3.33 (m, 1H), 3.71 (m, 1H), 3.85 (m, 1H), 4.00 (m, 2H), 4.26 (m, 2H), 4.55 (m, 1H), 5.03 (d, 1H), 5.14 (dd, 1H), 5.66 (bs, 1H), 5.80 (m, 1H), 6.42 (s, 1H), 6.54 (d, 1H), 6.59 (d, 1H), 6.63 (s, 1H), 6.94 (m, 1H), 7.40 (m, 1H), 7.52 (d,1H), 7.66 (d, 1H), 7.77 (s, 1H), 7.90 (m, 1H), 9.16 (bs, 1H), 9.16 (bs,1H) |
| 53 | 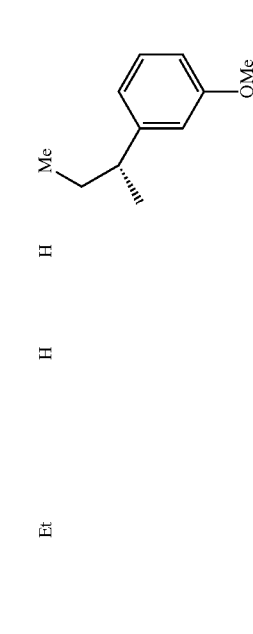 | Et | 3-F | 5-F | 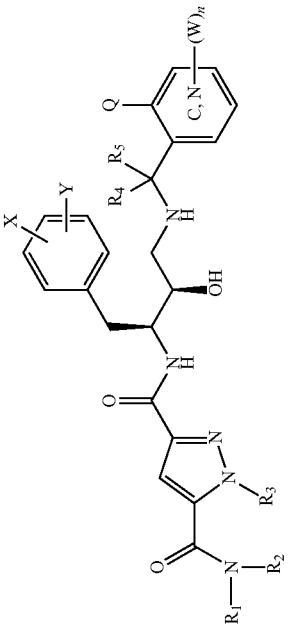 | 0.70-1.85 (m, 20H), 2.70 (m, 1H), 2.86 (m, 1H), 2.94 (m, 1H), 3.05 (d, 1H), 3.14 (m, 1H), 3.47 (m, 1H), 3.88 (m, 1H), 4.03 (m, 1H), 4.14 (m, 2H), 4.70 (m, 1H), 5.82 (bs, 1H), 6.58 (s, 1H), 6.92 (m, 3H), 7.55 (m, 1H), 7.68 (m, 1H), 7.81 (d, 1H), 7.93 (s, 1H), 8.09 (m, 1H), 9.37 (bs, 1H), 9.62 (bs, 1H) |
| 54 | 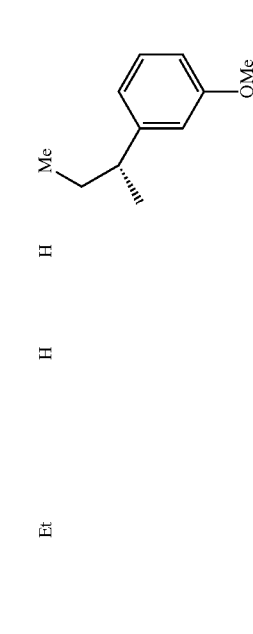 | Et | H | H | 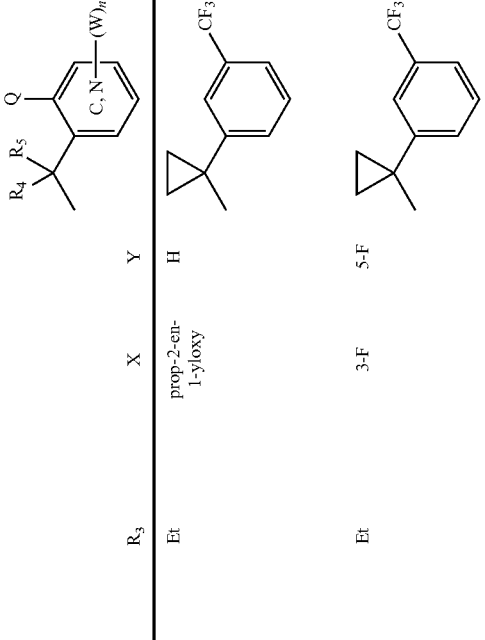 | 0.70-1.85 (m, 19H), 1.91 (m, 1H), 2.10 (m, 1H), 2.85 (m, 3H), 3.05 (d, 1H), 3.15 (m, 1H), 3.49 (m, 1H), 3.75 (s, 3H), 3.89 (m, 1H), 3.98 (m, 1H), 4.14 (m, 3H), 4.71 (m, 1H), 5.75 (d, 1H), 6.60 (s, 1H), 6.91 (d, 1H), 7.01 (d, 1H), 7.11 (m, 2H), 7.17 (m, 4H), 7.28 (m, 1H), 8.01 (d, 1H), 8.81 (bs, 1H), 9.20 (bs, 1H) |

TABLE 1-continued

| | NR₁R₂ | R₃ | X | Y | R₄ R₅ / Q,N-(W)ₙ | ¹H NMR δ ppm (500 MHz, DMSO-d₆) **If 600 MHz and DMSO-d₆ |
|---|---|---|---|---|---|---|
| 55 | N-methylpiperidine-propyl | Et | H | H | C(Me)(H)-3,5-bis(CF₃)phenyl | 0.70-1.80 (m, 19H), 2.80 (m, 2H), 2.98 (m, 2H), 3.07 (m, 1H), 3.41 (m, 1H), 3.87 (m, 1H), 3.95 (m, 1H), 4.11 (m, 2H), 4.63 (m, 2H), 5.74 (d, 1H), 6.52 (s, 1H), 7.03 (m, 1H), 7.10 (m, 4H), 8.00 (d, 1H), 8.11 (s, 1H), 8.23 (s, 2H), 8.94 (bs, 1H), 9.54 (bs, 1H) |
| 56 | N-methylpiperidine-propyl | Et | H | H | C(Me)(H)-3-OMe-phenyl | 0.60-1.85 (m, 19H), 2.79 (m, 3H), 2.99 (m, d, 1H), 3.08 (m, 1H), 3.41 (m, 1H), 3.68 (s, 3H), 3.82 (m, 1H), 3.94 (m, 1H), 4.09 (m, 2H), 4.29 (m, 1H), 4.64 (m, 1H), 5.69 (bs, 1H), 6.54 (s, 1H), 6.83 (d, 1H), 6.97 (d, 1H), 7.04 (m, 2H), 7.10 (m, 4H), 7.20 (m, 1H), 7.96 (m, 1H), 8.71 (bs, 1H), 9.21 (bs, 1H) |
| 57 | N-methylpiperidine-propyl | Et | H | H | C(Me)(H)-3-CF₃-phenyl | 0.55-1.70 (m, 19H), 2.71 (m, 2H), 2.80 (m, 1H), 2.91 (d, 1H), 3.00 (m, 1H), 3.34 (m, 1H), 3.77 (m, 1H), 3.87 (m, 1H), 4.01 (m, 2H), 4.42 (m, 1H), 4.56 (m, 1H), 5.65 (d, 1H), 6.45 (s, 1H), 6.96 (m, 1H), 7.02 (m, 4H), 7.48 (m, 1H), 7.59 (d, 1H), 7.69 (d, 1H), 7.80 (s, 1H), 7.90 (d, 1H), 8.80 (bs, 1H), 9.35 (bs, 1H) |

TABLE 1-continued

| # | NR₁R₂ | R₃ | X | Y | Substituent | ¹H NMR δ ppm (500 MHz, DMSO-d₆) **If 600 MHz and DMSO-d₆ |
|---|---|---|---|---|---|---|
| 58 | 1-methyl-2-(propyl)piperidine | Et | H | H | 7-methoxy-1,2,3,4-tetrahydronaphthalen-1-yl (methyl) | 0.7-1.85 (m, 17H), 1.90 (m, 1H), 2.02 (m, 2H), 2.63 (m, 1H), 2.68 (m, 1H), 2.90 (m, 2H), 3.10 (m, 3H), 3.47 (m, 1H), 3.71 (s, 3H), 3.95 (m, 1H), 4.14 (m, 3H), 4.52 (m, 1H), 4.71 (m, 1H), 5.92 (d, 1H), 6.00 (s, 1H), 6.83 (d, 1H), 7.06 (d, 1H), 7.16 (m, 6H), 8.15 (d, 1H), 8.69 (bs, 1H), 9.03 (bs, 1H) |
| 59 | 1-methyl-2-(propyl)piperidine | Et | H | H | 6-methoxy-2,3-dihydro-1H-inden-1-yl (methyl) | 0.70-1.85 (m, 16H), 2.15 (m, 1H), 2.45 (m, 1H), 2.77 (m, 1H), 2.89 (m, 2H), 2.98 (m, 2H), 3.11 (m, 2H), (m, 1H), 3.71 (s, 3H), 3.91 (m, 1H), 4.15 (m, 3H), 4.71 (m, 1H), 4.77 (m, 1H), 5.88 (bs, 1H), 6.60 (s, 1H), 6.87 (d, 1H), 7.18 (m, 7H), 8.12 (m, 1H), 8.91 (bs, 1H), 9.17 (bs, 1H) |
| 60 | 1-methyl-2-(propyl)piperidine | Et | H | H | 2-(3-methoxyphenyl)propan-2-yl | 0.70-1.85 (m, 19H), 2.77 (m, 2H), 2.84 (m, 1H), 3.06 (d, 1H), 3.14 (m, 1H), 3.47 (m, 1H), 3.71 (s, 3H), 3.83 (m, 1H), 4.06 (m, 1H), 4.13 (m, 2H), 4.32 (m, 1H), 4.70 (m, 1H), 5.84 (bs, 1H), 6.56 (s, 1H), 6.84 (d, 1H), 7.02 (d, 1H), 7.11 (m, 2H), 7.17 (m, 4H), 7.22 (m, 1H), 8.02 (d, 1H), 9.03 (bs, 2H) |

TABLE 1-continued (Iter)

| | NR₁R₂ | R₃ | X | Y | R₄,R₅ | ¹H NMR δ ppm (500 MHz, DMSO-d₆) **If 600 MHz and DMSO-d₆ |
|---|---|---|---|---|---|---|
| 61 | (1-methyl-piperidin-2-yl)ethyl group with CH₃ | Et | H | H | (R)-1-(3-methoxyphenyl)propyl with Me | ** 0.65 (t, 3H), 0.70-1.90 (m, 17H), 2.15 (m, 1H), 2.81 (m, 2H), 2.83 (m, 1H), 3.05 (d, 1H), 3.14 (m, 1H), 3.48 (m, 1H), 3.71 (s, 3H), 3.81 (m, 1H), 4.05 (m, 1H), 4.13 (m, 3H), 4.70 (m, 1H), 5.82 (d, 1H), 6.56 (s, 1H), 6.85 (d, 1H), 6.99 (d, 1H), 7.11 (m, 2H), 7.18 (m, 4H), 7.23 (m, 1H), 8.02 (m, 1H), 9.03 (bs, 2H) |
| 62 | 2-(1-methyl-piperidin-2-yl)ethyl group | Et | H | H | 6-methoxy-2,3-dihydro-1H-inden-1-yl with Me | **0.70-1.80 (m, 18H), 2.16 (m, 1H), 2.43 (m, 1H), 2.75 (m, 1H), 2.82 (m, 2H), 2.96 (m, 1H), 3.09 (m, 3H), 3.47 (m, 1H), 3.90 (m, 1H), 4.14 (m, 3H), 4.73 (m, 2H), 5.84 (bs, 1H), 6.63 (s, 1H), 6.88 (d, 1H), 7.12 (m, 1H), 7.21 (m, 6H), 8.10 (m, 1H), 8.89 (bs, 1H), 9.04 (bs, 1H) |

TABLE 1-continued
(Iter)
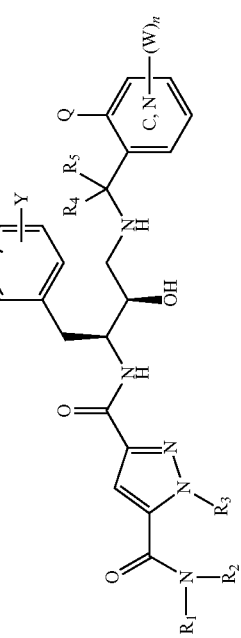
| | $NR_1R_2$ | $R_3$ | X | Y | | $^1$H NMR δ ppm (500 MHz, DMSO-$d_6$) **If 600 MHz and DMSO-$d_6$ |
|---|---|---|---|---|---|---|
| 63 | 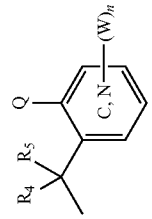 | Et | H | H | | **0.70-1.80 (m, 17H), 1.89 (m, 1H), 2.00 (m, 2H), 2.64 (m, 2H), 2.88 (m, 2H), 3.11 (m, 3H), 3.48 (m, 1H), 3.71 (s, 3H), 3.95 (m, 1H), 4.14 (m, 3H), 4.49 (m, 1H), 4.70 (m, 1H), 5.87 (bs, 1H), 6.62 (s, 1H), 6.85 (d, 1H), 7.07 (d, 1H), 7.12 (m, 2H), 7.23 (m, 4H), 8.08 (d, 1H), 8.74 (bs, 1H), 8.82 (bs, 1H) |
| 64 | 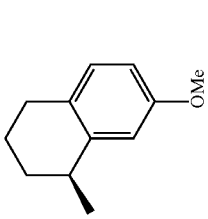 | Et | 3-F | 5-F | | 0.60-2.05 (m, 20H), 2.60 (m, 2H), 2.77 (m, 1H), 2.85 (m, 1H), 3.07 (m, 3H), 3.48 (m, 1H), 3.65 (s, 3H), 3.88 (m, 1H), 4.09 (m, 3H), 4.44 (m, 1H), 4.64 (m, 1H), 5.83 (bs, 1H), 6.59 (s, 1H), 6.79 (d, 1H), 6.92 (m, 3H), 7.03 (m, 2H), 8.17 (m, 1H), 8.70 (bs, 1H), 8.80 (bs, 1H) |

TABLE 1-continued (Iter)

[Structure of formula (Iter) shown]

| | NR₁R₂ | R₃ | X | Y | [Aryl group] | ¹H NMR δ ppm (500 MHz, DMSO-d₆) *If 600 MHz and DMSO-d₆ |
|---|---|---|---|---|---|---|
| 65 | [N-methylpiperidine with propyl chain] | Et | 3-F | 5-F | [tetrahydronaphthalene with CF₃, methyl] | 0.70-2.20 (m, 20H), 2.86 (m, 4H), 3.14 (m, 3H), 3.50 (m, 1H), 3.98 (m, 1H), 4.15 (m, 3H), 4.68 (m, 2H), 5.92 (d, 1H), 6.67 (s, 1H), 6.99 (m, 3H), 7.42 (d, 1H), 7.64 (d, 1H), 7.95 (s, 1H), 8.24 (d, 1H), 8.85 (bs, 1H), 9.00 (bs, 1H) |
| 66 | [N-methylpiperidine with CH₂OMe] | Et | H | H | [phenyl with CF₃, ethyl] | 1.36 (m, 4H), 1.66 (m, 5H), 2.88 (m, 2H), 3.10 (m, 2H), 3.21 (m, 4H), 3.48 (m, 1H), 3.73 (m, 1H), 3.92 (m, 1H), 4.12 (m, 4H), 4.27 (m, 3H), 5.90 (bs, 1H), 6.65 (s, 1H), 7.14 (m, 1H), 7.22 (m, 4H), 7.63 (m, 1H), 7.75 (d, 1H), 7.82 (d, 1H), 7.95 (s, 1H), 8.14 (d, 1H), 8.19 (bs, 1H), 9.00 (bs, 1H) |
| 67 | [N-methylpiperidine with CH₂OMe] | Et | 3-F | 5-F | [tetrahydronaphthalene with OMe, methyl] | **1.36 (m, 4H), 1.63 (m, 6H), 1.90 (m, 1H), 2.02 (m, 1H), 2.65 (m, 2H), 2.84 (m, 2H), 2.93 (m, 1H), 3.20 (m, 5H), 3.25 (s, 3H), 3.19 (m, 4H), 3.29 (s, 3H), 3.94 (m, 1H), 4.14 (m, 3H), 4.29 (m, 1H), 4.50 (m, 1H), 5.86 (d, 1H), 6.65 (s, 1H), 6.86 (d, 1H), 6.97 (m, 3H), 7.08 (d, 1H), 7.12 (s, 1H), 8.16 (d, 1H), 8.74 (bs, 1H), 8.83 (bs, 1H) |

*The exact stereochemistry at the level of the amide contine of compounds 34 and 35 has not been determined.

TABLE II (Iquater)

[Structure: Iquater general formula showing pyrazole core with R1-N(Ra)(Rb)-N-C(=O) group, R3 on pyrazole N, C(=O)-NH-CH(CH2-aryl(X,Y))-CH(OH)-CH2-NH-C(R4)(R5)-aryl(Q, C/N, (W)n)]

[Sub-structure shown: R4, R5, Q on C,N—(W)n aryl group]

| # | R1 | —NRaRb | R3 | X | Y | aryl group | data |
|---|----|----|----|---|---|---|------|
| 68 | H | 2,6-dimethylpiperidin-1-yl | Et | H | H | 3-(CF3)phenylmethyl | 0.97 (m, 6H), 1.32 (m, 6H), 1.66 (m, 3H), 2.51 (m, 1H), 2.61 (m, 1H), 2.89 (m, 2H), 3.11 (m, 2H), 3.95 (m, 1H), 4.13 (m, 1H), 4.28 (m, 2H), 4.51 (m, 2H), 5.94 (bs, 1H), 7.20 (m, 6H), 7.64 (t, 1H), 7.75 (d, 1H), 7.82 (d, 1H), 7.95 (s, 1H), 8.15 (d, 1H), 8.62 (bs, 1H), 9.09 (bs, 1H), 9.70 (bs, 1H) |
| 69 | H | N(CH3)(CH2Ph) | Et | H | H | 3-(CF3)phenylmethyl | 1.05 (t, 3H), 1.21 (t, 3H), 2.90 (m, 4H), 3.10 (m, 1H), 3.13 (m, 1H), 3.93 (m, 1H), 4.00 (m, 2H), 4.09 (m, 1H), 4.26 (m, 2H), 4.38 (m, 2H), 5.96 (bs, 1H), 6.95 (s, 1H), 7.12 (m, 1H), 7.24 (m, 5H), 7.29 (dd, 2H), 7.38 (d, 2H), 7.62 (m, 1H), 7.73 (d, 1H), 7.81 (d, 1H), 7.95 (s, 1H), 8.14 (d, 1H), 9.01 (bs, 1H), 9.25 (bs, 1H), 9.42 (s, 1H) |
| 70 | H | 2-methoxy-1-methylpyrrolidin-2-yl | Et | H | H | 3-(CF3)phenylmethyl | 1.27 (t, 3H), (m, 1H), (m, 2H), (m, 1H), 2.82 (m, 3H), 3.02 (m, 3H), 3.14 (m, 5H), 3.31 (m, 1H), 3.88 (m, 1H), 4.04 (m, 1H), 4.20 (m, 2H), 4.43 (m, 2H), 5.85 (bs, 1H), 7.02 (s, 1H), 7.06 (m, 1H), 7.13 (m, 4H), 7.57 (m, 1H), 7.68 (d, 1H), 7.75 (d, 1H), 7.88 (s, 1H), 8.09 (d, 1H), 8.93 (bs, 1H), 9.18 (bs, 1H), 9.55 (s, 1H) |
| 71 | H | N(CH3)(CH2Ph) | Et | 3-F | 5-F | 7-methoxytetralin-1-yl | 1.05 (t, 3H), 1.21 (t, 3H), 1.67 (m, 1H), 1.92 (m, 1H), 2.02 (m, 2H), 2.65 (m, 2H), 2.81 (m, 1H), 2.92 (m, 3H), 3.13 (m, 2H), 3.69 (s, 3H), 3.98 (m, 3H) 4.14 (m, 1H), 4.38 (m, 2H), 4.51 (m, 1H), 5.90 (bs, 1H), 6.87 (m, 1H), 6.96 (m, 4H), 7.09 (d, 1H), 7.15 (d, 1H), 7.23 (m, 1H), 7.28 (m, 2H), 7.38 (m, 2H), 8.23 (d, 1H), 8.85 (bs, 1H), 9.01 (bs, 1H), 9.44 (bs, 1H) |
| 72 | H | 2-methoxy-1-methylpyrrolidin-2-yl | Et | 3-F | 5-F | 7-methoxytetralin-1-yl | 1.27 (t, 3H), 1.40 (m, 1H), 1.65 (m, 3H), 1.85 (m, 2H), 1.95 (m, 2H), 2.58 (m, 2H), 2.84 (m, 3H), 3.09 (m, 7H), 3.30 (m, 1H), 3.64 (m, 4H), 3.90 (m, 1H), 4.07 (m, 1H), 4.43 (m, 3H), 5.85 (bs, 1H), 6.81 (m, 1H), 6.90 (m, 3H), 7.02 (m, 2H), 7.08 (s, 1H), 8.19 (d, 1H), 8.74 (bs, 1H), 8.89 (bs, 1H), 9.54 (s, 1H) |

The compounds of the invention underwent pharmacological testing, which demonstrated their usefulness as active substances in therapeutics.

In particular they were tested for their effects in inhibition of production of the (β-amyloid peptide (β-A4).

The β-amyloid peptide (β-A4) is a fragment of a more important precursor protein called APP (Amyloid Precursor Protein). The latter is produced and is present in various cells of animal and human tissue. However, its cleavage in brain tissue by enzymes of the protease type leads to the formation of the peptide β-A4 which accumulates in the form of amyloid plaque. The two proteases responsible for the production of the amyloid peptide are known as beta and gamma-secretases (M. S. Wolfe, J. Med. Chem., 2001, 44, 2039-60).

It has been shown that this progressive deposition of the peptide β-A4 is neurotoxic and might play an important role in Alzheimer's disease (C. Hölscher, Neurosciences, 2005, 16, 181-212).

Thus, the compounds of the present invention, as inhibitors of the production of the β-amyloid peptide (β-A4) by inhibition of beta-secretase BACE1 (β-site APP cleavage enzyme subtype 1), can be used in the treatment of pathologies such as senile dementia, Alzheimer's disease, Down's syndrome, Parkinson's disease, amyloid angiopathy, cerebrovascular disorders, and/or neurodegenerative diseases (F. Coria et al., Neuropath. Appl. Neurobiol., 1996, 22, 216-227).

The enzymatic activity of BACE1 and the production of the β-A4 peptide can be analyzed in vitro and in viva Various tests can be used for demonstrating the inhibitory activity of compounds on BACE1. Depending on circumstances, these tests can be performed with soluble BACE1 and a synthetic substrate, with cells expressing the substrate APP and BACE1 and/or with wild-type or transgenic animal models expressing APP and BACE1. The cells can be of various types, either transfected with the wild-type or mutated APP gene (CHO, HEK293, SHSY5Y, H4 etc.), or natural (IMR32, primary cultures of mouse neurons etc.). Similarly, tests of selectivity for cathepsin D and for alpha-secretase can be performed in particular (I. Hussain et al., Journal of Neurochemistry, 2007, 100, 802-809).

These tests are described according to the protocols given below.

Hereinafter:

DMSO=dimethylsulfoxide

DMEM/F12=Dulbecco's Modified Eagle's Medium/Ham nutrient mixture F12

Test 1: Inhibition of Soluble BACE1

This test uses soluble BACE1 and a synthetic substrate of BACE1.

The human recombinant soluble enzyme BACE1 is available from R&D Systems (reference 931-AS).

The synthetic peptide, made up of the amino acid sequence Ser-Glu-Val-Asn-Leu-Asp-Ala-Glu-Phe-Arg (S-10-R, available from NeoMPS, reference SP000122), is used as synthetic substrate of BACE1.

This synthetic substrate incorporates the cleavage site of BACE1 and fluorescent or chromogenic groups, so that the cleavage products can then be detected, either with UV after separation by HPLC, or by measurement of fluorescence or of optical density. In the present case, the cleavage product Asp-Ala-Glu-Phe-Arg, released during hydrolysis of S-10-R by BACE1, is quantified by UV detection [195 nm] after separation by HPLC with a gradient of acetonitrile from 2% to 100% [HP1100, Agilent; Column Atlantis dC18 (5 mm×2.1 mm; 3 µm)].

The synthetic substrate S-10-R is present at a final concentration of 350 µM, much lower than Km.

BACE1 is incubated at 20 nM in the presence of different concentrations of test compounds from 1 nM to 100 µM (the concentrations of inhibitors are tested starting from 100 µM by dilutions to a third), for 1 hour at 37° C., in a sodium acetate/acetic acid buffer 100 mM pH 4.5. The final concentration of DMSO in the test is 10%.

The percentage inhibition of the activity of BACE1 by the compounds of the invention is determined as a function of the amount of cleavage product detected by HPLC: the smaller the amount of cleavage product detected, the greater the inhibitory activity of the compounds.

The values of $IC_{50}$ are then calculated from the percentage inhibition previously determined, in relation to the concentration of the test compounds.

The most active compounds of formula (I) according to the present invention displayed an $IC_{50}$ less than 50 µM, preferably less than 10 µM, preferably less than 1 µM, preferably less than 100 nM. For example, compound 69 in the table had an $IC_{50}$ of 2 µM and compound 53 in the table had an $IC_{50}$ of 73 nM.

Test 2: Inhibition of Cellular Secretion of β-A4 40 and Soluble APPbeta with a Transfected Cell Line This test uses cells expressing the substrate APP and BACE1.

A stable line of HEK293 cells [M. Citron et al., Nature, 1992, 360, 672-674] over expressing the APP751 gene bearing the Swedish double mutation (Lys651Met652 in Asn651Leu652; numbering of APP751) is used. The cells are distributed at a density of 15000 cells per well in a 96-well plate and cultivated for 72 hours in a DMEM/Ham F12 culture medium containing 10% of inactivated fetal calf serum. After replacing the culture medium, the test compounds are added at various concentrations (1 nM to 10 µM); the concentrations of inhibitors are tested from 10 µM by dilutions to a third]. The final concentration of DMSO is 1%. The cells are cultivated for 24 hours in the presence of the test compounds. The viability of the cells is monitored with the MTS kit from Promega (G3581). The supernatants are collected and the concentrations of amyloid β-A4 40 and Swedish soluble APPbeta peptides are determined using commercial assay kits available from MSD (references K11FTE-2 and K111BUE-2). The inhibitory activity of the test compounds is calculated from the percentage inhibition of secretion of the peptides in relation to the concentration of the test compound.

Test 3: Selectivity with Respect to Cellular Secretion of Soluble APPalpha with a Transfected Cell Line The same type of test as test 2 is used.

Test 4: Inhibition of Cellular Secretion of β-A4 40 with a Natural Cell Line

A commercial human neuroblastoma line (ATTC No. CCL-127), IMR32, which expresses the substrate APP and BACE1 naturally, is used. The cells are distributed at a density of 80000 cells per well in a 96-well plate and cultivated for 24 hours in a DMEM/Ham F12 culture medium containing 10% of inactivated fetal calf serum. After replacing the culture medium, the test compounds are added at various concentrations (1 nM to 10 µM); the concentrations of inhibitors are tested from 10 µM by dilutions to a third]. The final concentration of DMSO is 1%. The cells are cultivated for 48 hours in the presence of the test compounds. The viability of the cells is monitored with the MTS kit from Promega (G3581). The supernatants are collected and the concentrations of amyloid peptide β-A4 40 are determined using the commercial assay kit available from MSD (reference K11FTE-2). The inhibitory activity of the test compounds is calculated from the percentage inhibition of secretion of the peptides in relation to the concentration of test compound.

The results of the biological tests show that the compounds are inhibitors of formation of the amyloid peptide (β-A4).

Thus, these compounds can be used in the treatment of pathologies in which an inhibitor of the formation of the β-amyloid peptide (β-A4) provides a therapeutic benefit. Such pathologies are notably senile dementia, Alzheimer's disease, Down's syndrome, Parkinson's disease, amyloid angiopathy, cerebrovascular disorders, and/or neurodegenerative diseases (F. Coria et al., Neuropath. Appl. Neurobiol., 1996, 22, 216-227).

The use of the compounds according to the invention for the preparation of a medicinal product intended for treating the pathologies mentioned above forms an integral part of the invention.

The invention also relates to medicinal products that comprise a compound of formula (I), or a salt of addition of the latter to a pharmaceutically acceptable acid or a hydrate or a solvate of the compound of formula (I). These medicinal products find application in therapeutics, notably in the treatment of the pathologies mentioned above.

According to another of its aspects, the present invention relates to pharmaceutical compositions containing, as active principle, at least one compound according to the invention. Said pharmaceutical compositions contain an effective dose of a compound according to the invention, or of a pharmaceutically acceptable salt, a hydrate or a solvate of said compound, and optionally one or more pharmaceutically acceptable excipients.

Said excipients are selected, depending on the pharmaceutical form and the desired method of administration, from the usual excipients that are known by a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or possibly its salt, its solvate or its hydrate, can be administered in a unit dosage form, mixed with conventional pharmaceutical excipients, to animals and to human beings for the prophylaxis or treatment of the disorders or diseases mentioned above.

Suitable unit dosage forms include the forms for administration by the oral route such as tablets, soft or hard capsules, powders, granules, chewing gums and oral solutions or suspensions, forms for sublingual, buccal, intratracheal, intraocular, or intranasal administration, administration by inhalation, forms for subcutaneous, intramuscular or intravenous administration and forms for rectal or vaginal administration. For topical application, the compounds according to the invention can be used in creams, ointments or lotions.

As an example, a unit dosage form of a compound according to the invention in the form of a tablet can include the following ingredients:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropyl methylcellulose | 2.25 mg |
| Magnesium stearate | 3.0 mg |

In order to obtain the desired prophylactic or therapeutic effect, the dose of active principle can vary between 0.1 mg and 200 mg per kg of body weight per day. Although these dosages are examples of the average situation, there may be particular instances in which higher or lower dosages are appropriate, and said dosages also fall within the scope of the invention. In accordance with the usual practice, the dosage that is appropriate for each patient is determined by the doctor depending on the method of administration, and said patient's weight and response.

Each unit dose can contain from 0.1 to 1000 mg, preferably from 0.1 to 500 mg, of active principle in combination with one or more pharmaceutical excipients. This unit dose can be administered once to 5 times daily so as to administer a daily dosage from 0.5 to 5000 mg, preferably from 0.5 to 2500 mg.

According to another of its aspects, the present invention also relates to a method of treatment of the pathologies mentioned above which comprises the administration of a compound according to the invention, a pharmaceutically acceptable salt or a hydrate of said compound.

What is claimed is:
1. A compound of the following formula (I):

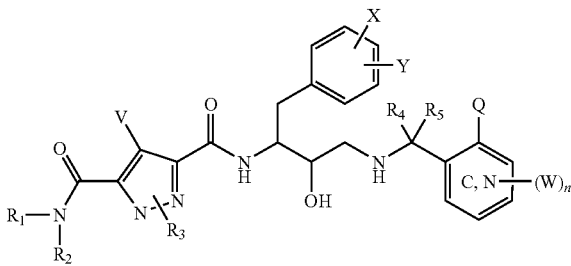

in which $R_1$ represents a hydrogen atom, a $C_{3-6}$-cycloalkyl group, or a $C_{1-6}$-alkyl group, said $C_{1-6}$-alkyl optionally being substituted with one or more groups selected from hydroxy, $C_{1-6}$-alkoxy, halogen, $CF_3$, and $OCF_3$;

$R_2$ represents a hydrogen atom, a $C_{1-10}$-alkyl group, an aryl group, or an $NR_aR_b$ group, said $C_{1-10}$-alkyl group and aryl group optionally being substituted with one or more groups selected from hydroxy, $C_{1-6}$-alkyl, $C_{1-6}$-alkoxy, halogen, $CF_3$ and $OCF_3$, it being understood that at least one of $R_1$ or of $R_2$ is not a hydrogen atom;

or alternatively $R_1$ and $R_2$ form, together with the nitrogen atom to which they are attached, a heterocyclic group, said heterocyclic group optionally being substituted with one or more groups selected from hydroxy, $C_{1-6}$-alkyl, $C_{1-6}$-alkylene-O—$C_{1-6}$-alkyl, $C_{1-6}$-alkoxy, halogen, $CF_3$ and $OCF_3$; wherein $R_a$ and $R_b$ represent, independently of one another, a hydrogen atom, a $C_{1-6}$-alkyl group, an aryl, $C_{1-6}$-alkylene-aryl or $C_{1-6}$-alkylene-heteroaryl group, said $C_{1-6}$-alkyl, aryl, $C_{1-6}$-alkylene-aryl or $C_{1-6}$-alkylene-heteroaryl group optionally being substituted with one or more groups selected from hydroxy, $C_{1-6}$-alkyl, $C_{1-6}$-alkoxy, halogen, $CF_3$ and $OCF_3$, or alternatively $R_a$ and $R_b$ form, together with the nitrogen atom to which they are attached, a heterocycle, said heterocycle optionally being substituted with one or more groups selected from $C_{1-6}$-alkyl, $C_{1-6}$-alkylene-O—$C_{1-6}$-alkyl, $C_{1-6}$-alkoxy, halogen, $CF_3$ and $OCF_3$;

$R_3$, joined to the rest of the molecule by one of the two nitrogen atoms of the pyrazolyl, represents a group selected from:

$C_{1-6}$-alkyl, aryl, $C_{1-6}$-alkylene-aryl or $C_{1-6}$-alkylene-heteroaryl, said alkyl, aryl and heteroaryl groups optionally being substituted with one or more groups selected from a halogen atom, —CN, —$OR_6$, —$NR_6R_7$, —$CONR_6R_7$, —$NR_6COR_7$, and —$COOR_6$ in which:

$R_6$ and $R_7$ represent, independently of one another, a hydrogen atom, or a $C_{1-6}$-alkyl group;

$R_4$ and $R_5$ represent, independently of one another, a hydrogen atom, or a $C_{1-6}$-alkyl group, or alternatively $R_4$ and $R_5$ form, together with the carbon atom to which they are attached, a spirocycle containing from 3 to 6 carbon atoms;

or alternatively $R_4$ and $R_5$ form together, and with the carbon chain to which they are attached, a saturated ring having 3 or 5 carbon atoms and an oxygen atom, said ring optionally being substituted with one or more groups R, the group or groups R representing, independently of one another, a halogen atom, a $C_{1-3}$-alkyl, or $C_{1-3}$-alkoxy group, or alternatively two groups R, carried by the same carbon atom, together form an oxo group;

Q represents a hydrogen or halogen atom, a group $CF_3$, $OCHF_2$, $OCF_3$, $C_{1-6}$-alkoxy, $C_{3-6}$-cycloalkyl or —O—$C_{3-6}$-cycloalkyl, said groups optionally being substituted with one or more groups selected from a halogen atom, a hydroxy and $OCF_3$ group, or alternatively Q and $R_5$ form together, and with the carbon chain to which they are attached, a saturated carbon ring having 5 or 6 carbon atoms, said ring optionally being substituted with one or two groups R, the group or groups R representing, independently of one another, groups selected from a halogen atom, $OCHF_2$, $OCF_3$, a $C_{1-3}$-alkyl and $C_{1-3}$-alkoxy group;

or alternatively Q and $R_5$ form together, and with the carbon chain to which they are attached, a saturated ring having 4 or 5 carbon atoms and a heteroatom such as O, S or N, said ring and the heteroatom N optionally being substituted with one or more groups R, the group or groups R representing, independently of one another, groups selected from a halogen atom, $OCHF_2$, $OCF_3$, a $C_{1-3}$-alkyl and $C_{1-3}$-alkoxy group, or alternatively two groups R, carried by the same carbon atom, together form an oxo group;

X and Y represent, independently of one another, a hydrogen atom, a halogen atom, a $C_{1-6}$-alkoxy, —O—$C_{2-6}$-alkenyl, —O-aryl, —O—$C_{1-6}$-alkyl-aryl, —$CF_3$, —$OCF_3$, or $C_{1-6}$-alkyl group;

V represents a hydrogen atom, a halogen atom, or a $C_{1-4}$-alkyl group;

n represents an integer selected from 0, 1, 2 and 3; and

W represents a hydrogen atom, a halogen atom, $COOR_6$, $CF_3$, $OCHF_2$, $OCF_3$, a $C_{1-6}$-alkyl, $C_{1-6}$-alkoxy group, $C_{3-6}$-cycloalkyl heterocycle, or an —O—$C_{3-6}$-cycloalkyl group, said groups optionally being substituted with one or more groups selected from a halogen atom, a hydroxy, $OCF_3$, and $C_{1-6}$-alkyl group, it being understood that when n is 2 or 3, the two or three groups W represent, independently of one another, the definitions given above;

or a salt, or an enantiomer, or a diastereoisomer or a mixture thereof.

2. The compound according to claim 1 having the formula (I-bis):

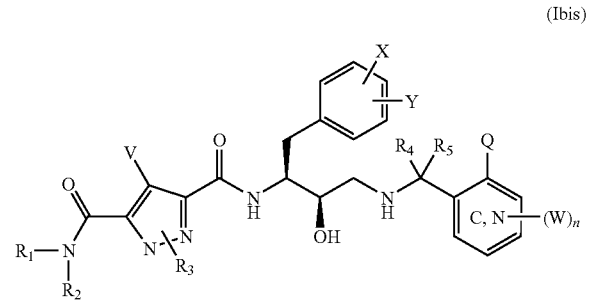

(Ibis)

in which $R_1$, $R_2$, $R_3$, $R_4$, $R_5$, X, Y, n, Q, V and W are as defined in claim 1, or a salt, or an enantiomer, or a diastereoisomer or a mixture thereof.

3. The compound according to claim 1 having the formula (I-ter):

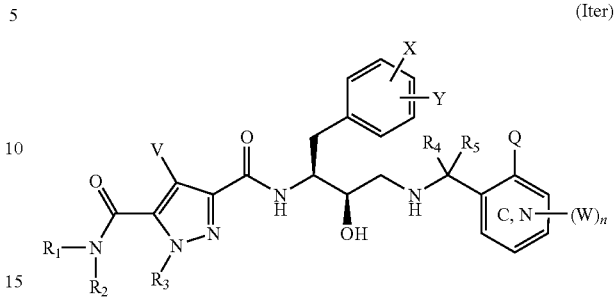

(Iter)

in which $R_1$, $R_2$, $R_3$, $R_4$, $R_5$, X, Y, n, Q, V and W are as defined in claim 1, or a salt, or an enantiomer, or a diastereoisomer or a mixture thereof.

4. The compound according to claim 1 having the formula (I-quater):

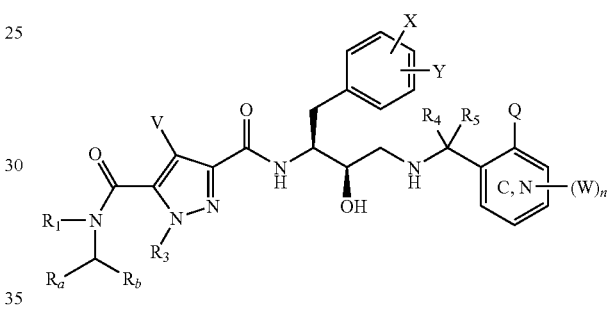

(Iquater)

in which $R_1$, $R_2$, $R_3$, $R_4$, $R_5$, X, Y, n, Q, V and W are as defined in claim 1, or a salt, or an enantiomer, or a diastereoisomer or a mixture thereof.

5. The compound of formula (I) according to claim 1, wherein:

$R_1$ represents a hydrogen atom, a $C_{3-6}$-cycloalkyl group, or an $C_{1-6}$-alkyl group, said $C_{1-6}$-alkyl optionally being substituted with one or more groups selected from a hydroxy, and $C_{1-6}$-alkoxy;

$R_2$ represents a hydrogen atom, a $C_{1-10}$-alkyl group, or a phenyl group, said group $C_{1-10}$-alkyl and phenyl optionally being substituted with one or more groups selected from hydroxy, $C_{1-6}$-alkyl, and $C_{1-6}$-alkoxy;

it being understood that at least one of $R_1$ or $R_2$ is not a hydrogen atom;

or $R_2$ represents a group $NR_aR_b$ in which:

$R_a$ and $R_b$ represent, independently of one another, a hydrogen atom, a $C_{1-6}$-alkyl group, an aryl, $C_{1-6}$-alkylene-aryl or $C_{1-6}$-alkylene-heteroaryl group, said $C_{1-6}$-alkyl, aryl, $C_{1-6}$-alkylene-aryl or $C_{1-6}$-alkylene-heteroaryl group optionally being substituted with one or more groups selected from hydroxy, $C_{1-6}$-alkyl, $C_{1-6}$-alkoxy, halogen, $CF_3$ and $OCF_3$, or alternatively $R_a$ and $R_b$ form, together with the nitrogen atom to which they are attached, a heterocycle, said heterocycle optionally being substituted with one or more groups selected from $C_{1-6}$-alkyl, $C_{1-6}$-alkylene-O—$C_{1-6}$-alkyl, $C_{1-6}$-alkoxy, halogen, $CF_3$ and $OCF_3$;

or alternatively $R_1$ and $R_2$ form, together with the nitrogen atom to which they are attached, a heterocyclic group, said heterocyclic group optionally being substituted with one or more groups selected from $C_{1-6}$-alkyl, $C_{1-6}$-alkoxy, and $C_{1-6}$-alkylene-O—$C_{1-6}$-alkyl;

$R_3$ represents a $C_{1-6}$-alkyl group or a benzyl group;

$R_4$ and $R_5$ represent, independently of one another, a hydrogen atom, or a $C_{1-6}$-alkyl group, or alternatively $R_4$ and $R_5$ form, together with the carbon atom to which they are attached, a spirocycle containing from 3 to 5 carbon atoms;

Q represents a hydrogen atom, or a $C_{1-3}$-alkyl group;

or alternatively Q and $R_5$ form together, and with the carbon chain to which they are attached, a saturated carbon ring having 5 or 6 carbon atoms, said ring optionally being substituted with one or two groups R, the group or groups R being, independently of one another, selected from a halogen atom, a $C_{1-3}$-alkyl, $OCHF_2$, $OCF_3$, $CF_3$ and $C_{1-3}$-alkoxy group;

or alternatively Q and $R_5$ form together, and with the carbon chain to which they are attached, a saturated ring having 4 or 5 carbon atoms and an oxygen atom, said ring optionally being substituted with one or two groups R, the group or groups R being, independently of one another, selected from a halogen atom, a $C_{1-3}$-alkyl, $OCHF_2$, $OCF_3$, $CF_3$ and $C_{1-3}$-alkoxy group;

X and Y represent, independently of one another, a hydrogen atom, a halogen atom, an —O—$C_{2-6}$-alkenyl, or —O-benzyl group;

n represents an integer selected from 1 or 2;

V represents a hydrogen atom; and

W represents a halogen atom, a $CF_3$, $C_{1-6}$-alkyl, —COOH, or a $C_{1-6}$-alkoxy group;

it being understood that when n is 2 or 3, the two or three groups W represent, independently of one another, the definitions given above, or a salt, or an enantiomer, or a diastereoisomer or a mixture thereof.

6. A method of preparation of a compound of formula (I) according to claim 1 comprising:

reacting a compound of formula (II):

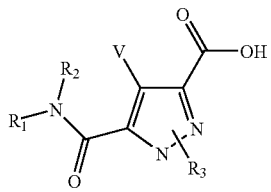

(II)

in which $R_1$, $R_2$, $R_3$ and V are as defined in claim 1, in an inert solvent, with a compound of formula (III):

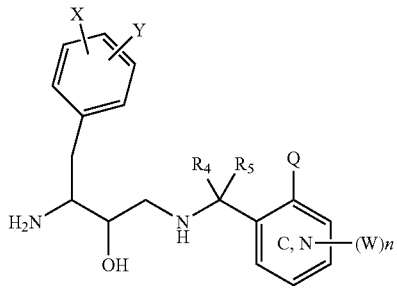

(III)

in which X, Y, $R_4$, $R_5$, Q, W and n are as defined in claim 1, at a temperature in the range of from about 0° C. to room temperature, to obtain the compound of formula (I) according to claim 1.

7. A pharmaceutical composition comprising at least one compound of formula (I) according to claim 1 or a pharmaceutically acceptable salt thereof and at least one pharmaceutically acceptable excipient.

8. A pharmaceutical composition comprising at least one compound of formula (I) according to claim 2 or a pharmaceutically acceptable salt thereof and at least one pharmaceutically acceptable excipient.

9. A pharmaceutical composition comprising at least one compound of formula (I) according to claim 3 or a pharmaceutically acceptable salt thereof and at least one pharmaceutically acceptable excipient.

10. A pharmaceutical composition comprising at least one compound of formula (I) according to claim 4 or a pharmaceutically acceptable salt thereof and at least one pharmaceutically acceptable excipient.

11. A pharmaceutical composition comprising at least one compound of formula (I) according to claim 5 or a pharmaceutically acceptable salt thereof and at least one pharmaceutically acceptable excipient.

12. A method for the treatment of a pathology in which an inhibitor of the formation of the β-amyloid peptide β-A4 provides a therapeutic benefit in a patient comprising administering to said patient a therapeutically effective amount of a compound of formula (I) according to claim 1 or a pharmaceutically acceptable salt thereof.

13. A method for the treatment of a pathology in which an inhibitor of the formation of the β-amyloid peptide β-A4 provides a therapeutic benefit in a patient comprising administering to said patient a therapeutically effective amount of a compound of formula (I) according to claim 2 or a pharmaceutically acceptable salt thereof.

14. A method for the treatment of a pathology in which an inhibitor of the formation of the β-amyloid peptide β-A4 provides a therapeutic benefit in a patient comprising administering to said patient a therapeutically effective amount of a compound of formula (I) according to claim 3 or a pharmaceutically acceptable salt thereof.

15. A method for the treatment of a pathology in which an inhibitor of the formation of the β-amyloid peptide β-A4 provides a therapeutic benefit in a patient comprising administering to said patient a therapeutically effective amount of a compound of formula (I) according to claim 4 or a pharmaceutically acceptable salt thereof.

16. A method for the treatment of a pathology in which an inhibitor of the formation of the β-amyloid peptide β-A4 provides a therapeutic benefit in a patient comprising administering to said patient a therapeutically effective amount of a compound of formula (I) according to claim 5 or a pharmaceutically acceptable salt thereof.

17. A method for the treatment of a disease in a patient, which disease is selected from the group consisting of senile dementia, Alzheimer's disease, Down's syndrome, Parkinson's disease, amyloid angiopathy, cerebrovascular disorders and neurodegenerative disease comprising administering to said patient a therapeutically effective amount of a compound of formula (I) according to claim 1 or a pharmaceutically acceptable salt thereof.

18. A method for the treatment of a disease in a patient, which disease is selected from the group consisting of senile dementia, Alzheimer's disease, Down's syndrome, Parkinson's disease, amyloid angiopathy, cerebrovascular disorders and neurodegenerative disease comprising administering to said patient a therapeutically effective amount of a compound of formula (I) according to claim 2 or a pharmaceutically acceptable salt thereof.

19. A method for the treatment of a disease in a patient, which disease is selected from the group consisting of senile dementia, Alzheimer's disease, Down's syndrome, Parkinson's disease, amyloid angiopathy, cerebrovascular disorders and neurodegenerative disease comprising administering to said patient a therapeutically effective amount of a compound of formula (I) according to claim 3 or a pharmaceutically acceptable salt thereof.

20. A method for the treatment of a disease in a patient, which disease is selected from the group consisting of senile dementia, Alzheimer's disease, Down's syndrome, Parkinson's disease, amyloid angiopathy, cerebrovascular disorders and neurodegenerative disease comprising administering to said patient a therapeutically effective amount of a compound of formula (I) according to claim 4 or a pharmaceutically acceptable salt thereof.

21. A method for the treatment of a disease in a patient, which disease is selected from the group consisting of senile dementia, Alzheimer's disease, Down's syndrome, Parkinson's disease, amyloid angiopathy, cerebrovascular disorders and neurodegenerative disease comprising administering to said patient a therapeutically effective amount of a compound of formula (I) according to claim 5 or a pharmaceutically acceptable salt thereof.

* * * * *

UNITED STATES PATENT AND TRADEMARK OFFICE
CERTIFICATE OF CORRECTION

PATENT NO.        : 9,102,628 B2
APPLICATION NO.   : 12/647056
DATED             : August 11, 2015
INVENTOR(S)       : Yann Foricher et al.

It is certified that error appears in the above-identified patent and that said Letters Patent is hereby corrected as shown below:

Title page, item (56):

On page 2, left-hand column, line 6: please replace: "Synthesisi" with --Synthesis--;

On page 2, right-hand column, line 9: please replace "Angiopathiss," with --Angiopathies,--.

In the claims:

At column 81, claim number 1, line number 7, please replace: "OCF$_3$, C$_{1-6}$-alkoxy," with --OCF$_3$, C$_{1-6}$-alkyl, C$_{1-6}$-alkoxy,--;

Signed and Sealed this
Twenty-sixth Day of July, 2016

Michelle K. Lee
*Director of the United States Patent and Trademark Office*

CERTIFICATE OF CORRECTION (continued)
U.S. Pat. No. 9,102,628 B2

At column 81, claim number 2, lines 51-62, formula (Ibis), please replace:

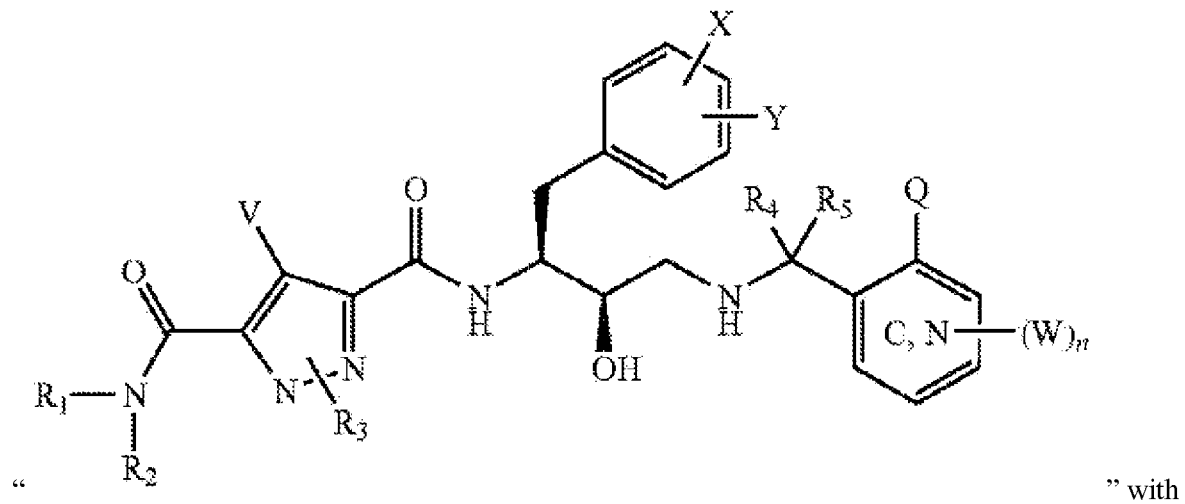

" with

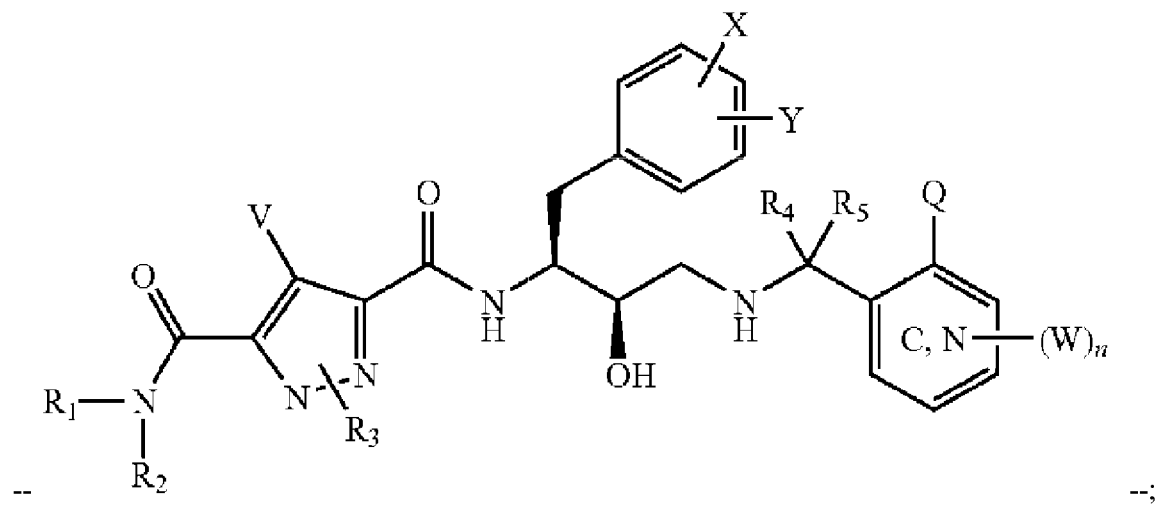

--;

CERTIFICATE OF CORRECTION (continued)
U.S. Pat. No. 9,102,628 B2

At column 82, claim number 3, lines 5-16, formula (Iter), please replace

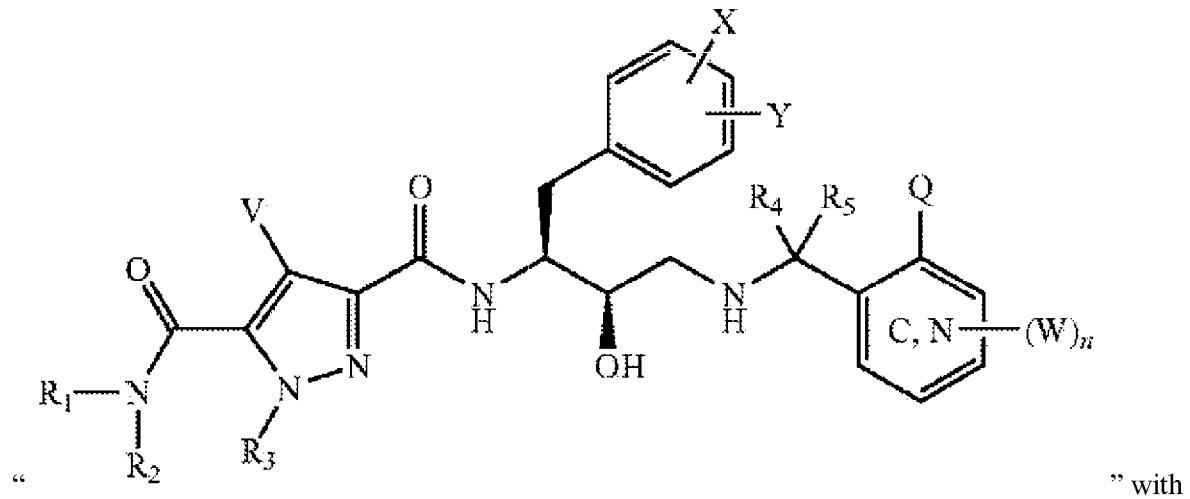

" with

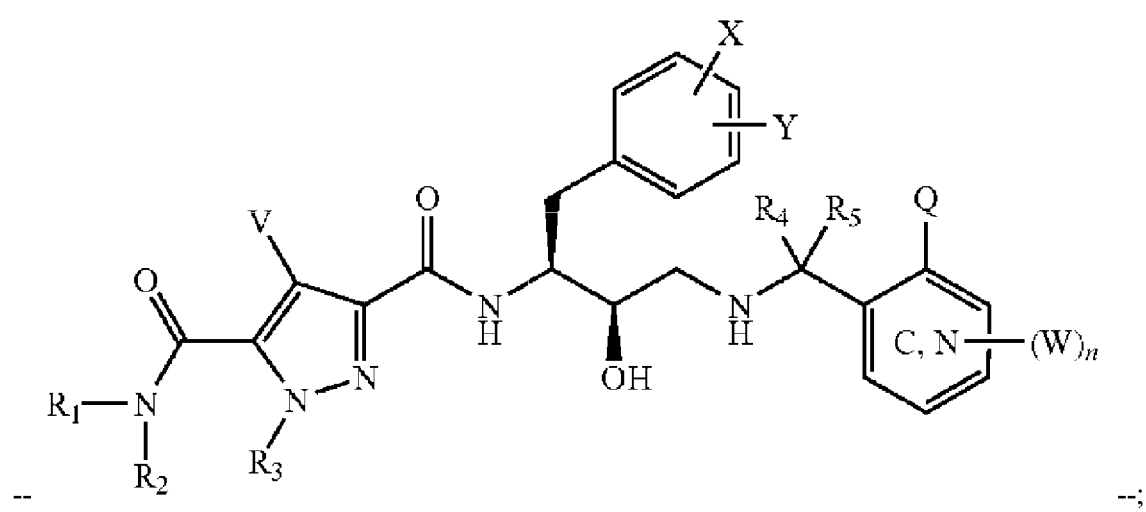

--;

CERTIFICATE OF CORRECTION (continued)
U.S. Pat. No. 9,102,628 B2

At column 82, claim number 4, lines 23-35, formula (Iquater), please replace:

(Iquater)

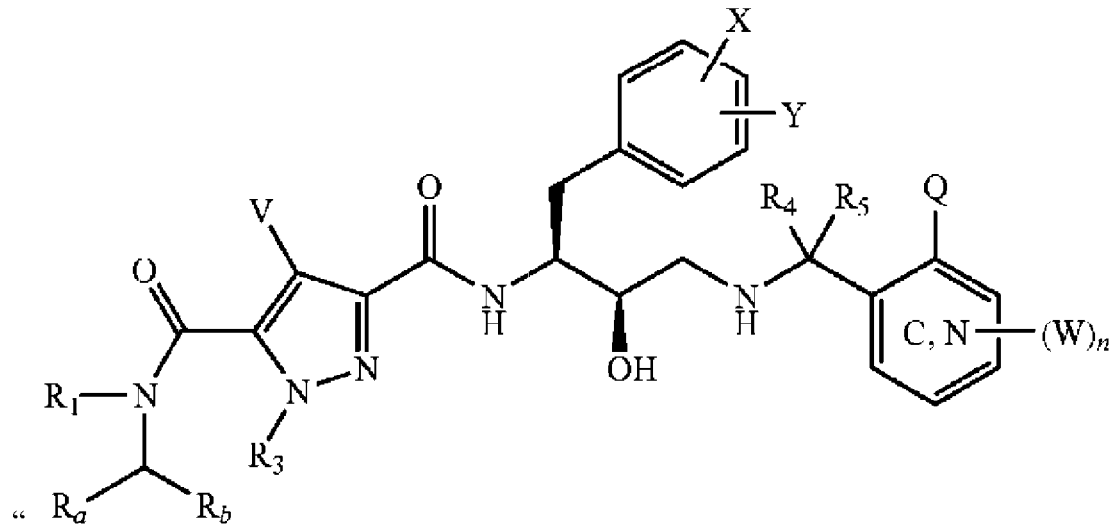

" with (I-quater)

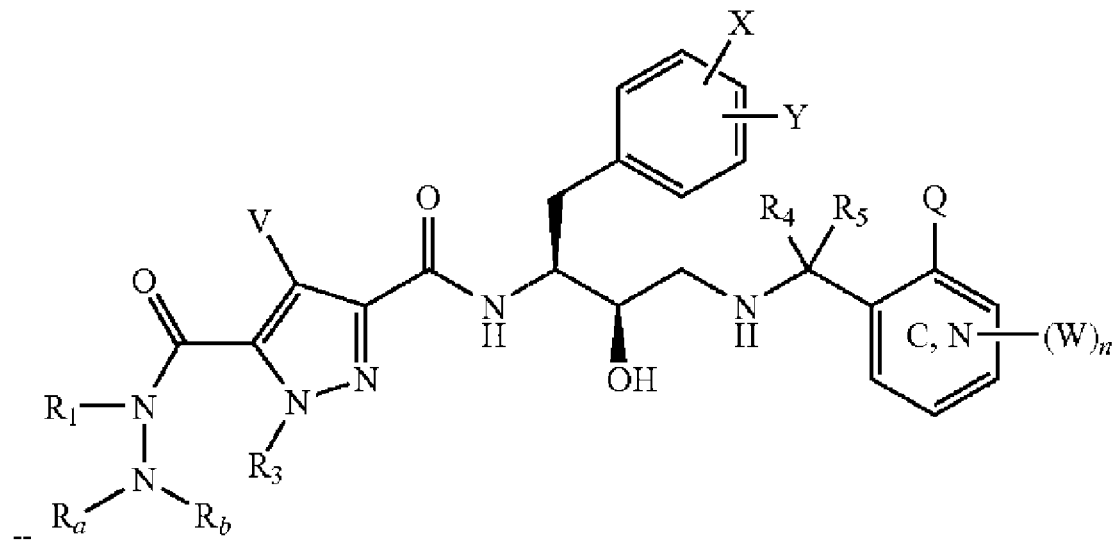

--; and

At Column 82, claim number 5, line number 43, please replace "an $C_{1-6}$-alkyl group," with --a $C_{1-6}$-alkyl group,--.